(12) United States Patent
Corum et al.

(10) Patent No.: US 11,693,070 B2
(45) Date of Patent: Jul. 4, 2023

(54) FUNCTIONAL MAGNETIC RESONANCE IMAGING WITH DIRECT DIPOLE DECOMPOSITION

(71) Applicant: CHAMPAIGN IMAGING LLC, Shoreview, MN (US)

(72) Inventors: Curtis A. Corum, Shoreview, MN (US); Carl J. Snyder, Shoreview, MN (US)

(73) Assignee: Champaign Imaging LLC, Shoreview, MN (US)

( * ) Notice: Subject to any disclaimer, the term of this patent is extended or adjusted under 35 U.S.C. 154(b) by 329 days.

(21) Appl. No.: 16/803,288

(22) Filed: Feb. 27, 2020

(65) Prior Publication Data

US 2020/0191892 A1    Jun. 18, 2020

Related U.S. Application Data

(63) Continuation of application No. PCT/US2018/059582, filed on Nov. 7, 2018.

(60) Provisional application No. 62/582,356, filed on Nov. 7, 2017.

(51) Int. Cl.
*G01R 33/48*  (2006.01)
*G01R 33/36*  (2006.01)
*G01R 33/54*  (2006.01)
*G01R 33/563*  (2006.01)

(52) U.S. Cl.
CPC ..... *G01R 33/4806* (2013.01); *G01R 33/3642* (2013.01); *G01R 33/4824* (2013.01); *G01R 33/543* (2013.01); *G01R 33/56341* (2013.01); *G01R 33/56366* (2013.01)

(58) Field of Classification Search
CPC ........... G01R 33/4806; G01R 33/3642; G01R 33/4824; G01R 33/543; G01R 33/56341; G01R 33/56366; G01R 33/34076; G01R 33/3415; G01R 33/56509; A61B 5/0046;
(Continued)

(56) References Cited

U.S. PATENT DOCUMENTS

| | | |
|---|---|---|
| 4,858,128 A | 8/1989 | Nowak |
| 4,937,526 A | 6/1990 | Ehman et al. |
| 5,287,276 A | 2/1994 | Crawford et al. |

(Continued)

FOREIGN PATENT DOCUMENTS

WO    2009107010    9/2009

OTHER PUBLICATIONS

Qin et al., Prospective head-movement correction for high-resolution MRI using an in-bore optical tracking system, Magn Reson Med., Oct. 2009, 2 pages.

(Continued)

*Primary Examiner* — Farhana A Hoque
(74) *Attorney, Agent, or Firm* — Dicke, Billig & Czaja, PLLC

(57) ABSTRACT

A system includes a machine readable storage medium storing instructions and a processor to execute the instructions. The processor executes the instructions to receive radial k-space magnetic resonance imaging (MRI) data of a patient and determine a series of dipole sources via direct dipole decomposition of the radial k-space MRI data. The processor executes the instructions to identify an activation within the patient based on the series of dipole sources.

20 Claims, 19 Drawing Sheets

(58) Field of Classification Search
CPC ... A61B 2576/026; A61B 5/055; G16H 30/40
USPC ......................................................... 324/322
See application file for complete search history.

(56) References Cited

U.S. PATENT DOCUMENTS

| | | | |
|---|---|---|---|
| 5,352,979 | A | 10/1994 | Conturo |
| 5,408,178 | A | 4/1995 | Wikswo, Jr. et al. |
| 5,545,993 | A | 8/1996 | Taguchi et al. |
| 5,552,605 | A | 9/1996 | Arata |
| 5,603,322 | A | 2/1997 | Jesmanowicz et al. |
| 5,850,486 | A | 12/1998 | Maas, III et al. |
| 5,953,439 | A | 9/1999 | Ishihara et al. |
| 6,057,685 | A | 5/2000 | Zhou |
| 6,104,943 | A | 8/2000 | Frederick et al. |
| 6,114,852 | A | 9/2000 | Zhou et al. |
| 6,292,683 | B1 | 9/2001 | Gupta et al. |
| 6,307,369 | B1 | 10/2001 | Felmlee et al. |
| 6,356,781 | B1 | 3/2002 | Lee et al. |
| 6,470,202 | B2 | 10/2002 | Rosenfeld |
| 6,477,398 | B1 | 11/2002 | Mills |
| 6,658,280 | B1 | 12/2003 | Haacke |
| 7,002,342 | B2 | 2/2006 | Duerk et al. |
| 7,457,655 | B2 | 11/2008 | Welch et al. |
| 7,598,739 | B2 * | 10/2009 | Vaughan, Jr. .... G01R 33/34046 324/318 |
| 8,422,756 | B2 | 4/2013 | Haacke et al. |
| 8,653,816 | B2 | 2/2014 | Lake et al. |
| 8,798,340 | B2 | 8/2014 | Corum et al. |
| 8,886,283 | B1 | 11/2014 | Chen et al. |
| 9,008,396 | B2 | 4/2015 | Haacke |
| 2008/0200799 | A1 | 8/2008 | Willard et al. |
| 2009/0009167 | A1 * | 1/2009 | Du ....................... G01R 33/561 324/307 |
| 2010/0321085 | A1 | 12/2010 | Jesmanowicz |
| 2013/0069648 | A1 | 3/2013 | Grodzki |
| 2014/0232393 | A1 * | 8/2014 | Wheaton ................ G01R 33/24 324/309 |

OTHER PUBLICATIONS

Mendes et al., Rigid-body motion correction with self-navigation MRI, Magn Reson Med., Mar. 2009, 2 pages.
Stone et al., Accelerating Advanced MRI Reconstructions on GPUs, J Parallel Distrib Comput., Oct. 2008, 2 pages.
Kim et al., Automatic correction of in-plane bulk motion artifacts in self-navigated radial MRI, Magn Reson Imaging, Apr. 2008, 2 pages.
Winkelmann et al., An optimal radial profile order based on the Golden Ratio for time-resolved MRI, IEEE Trans Med Imaging, Jan. 2007, 2 pages.
Jung et al., Consistent non-cartesian off-axis MRI quality: calibrating and removing multiple sources of demodulation phase errors, Magn Reson Med., Jan. 2007, 2 pages.
Rahmer et al., Three-dimensional radial ultrashort echo-time imaging with T2 adapted sampling, Magn Reson Med., May 2006, 2 pages.
Liu et al., Generation and visualization of four-dimensional MR angiography data using an undersampled 3-D projection trajectory, IEEE Trans Med Imaging, Feb. 2006, 2 pages.
Welch et al., Self-navigated motion correction using moments of spatial projections in radial MRI, Magn Reson Med., Aug. 2004, 2 pages.
Peters et al., Centering the projection reconstruction trajectory: reducing gradient delay errors, Magn Reson Med., Jul. 2003, 2 pages.
Rath et al., Between- and within-site variability of fMRI localizations., Hum Brain Mapp 37 : 2016, pp. 2151-2160.
Chen et al., Individual Variability and Test-Retest Reliability Revealed by Ten Repeated Resting-State Brain Scans over One Month., PLoS One 10 : e0144963, 2015, 16 pages.
Poldrack et al., Scanning the horizon: towards transparent and reproducible neuroimaging research., Nature reviews. Neuroscience 18 : 2017, 26 pages.
Nichols et al., Best Practices in Data Analysis and Sharing in Neuroimaging using MRI, bioRxiv . PMID: http://dx.doi.org/10.1101/054262, 2016, 71 pages.
Poldrack et al., Guidelines for reporting an fMRI study., Neuroimage 40 : 2008, 15 pages.
Haacke et al., Susceptibility weighted imaging (SWI)., Magnetic resonance in medicine 52 : 612-618, 2004, 11 pages.
Hagberg et al., Challenges for detection of neuronal currents by MRI., Magn Reson Imaging 24 : 483-493, 2006, 3 pages.
Cassara et al., Realistic simulations of neuronal activity: A contribution to the debate on direct detection of neuronal currents by MRI, NeuroImage 39 : 87-106, 2008, 2 pages.
Hagberg et al., Phase stability in fMRI time series: effect of noise regression, off-resonance correction and spatial filtering techniques , Neuroimage 59 : 3748-3761, 2012, 2 pages.
Balla et al., Functional quantitative susceptibility mapping (fQSM)., Neuroimage 100 : 112-124, 2014, 1 pge.
Calhoun et al., Independent component analysis of fMRI data in the complex domain., Magn Reson Med 48 : 180-192, 2002, 15 pages.
Arja et al., Changes in fMRI magnitude data and phase data observed in block-design and event-related tasks., NeuroImage 49 : 3149-3160, 2010, 19 pages.
Chen et al., In: Pelc, N. J.; Samei, E. & Nishikawa, R. M. (Ed.), Voxel magnetic field disturbance from remote vasculature in BOLD fMRI, SPIE-Intl Soc Optical Eng, 2011, 2 pages.
Chen et al., A computational multiresolution BOLD fMRI model, IEEE Trans Biomed Eng 58 : 2995-2999, 2011, 12 pages.
Chen et al., Two pitfalls of BOLD fMRI magnitude-based neuroimage analysis: non-negativity and edge effect., J Neurosci Methods 199 : 363-369, 2011, 14 pages.
Chen et al., Computed inverse resonance imaging for magnetic susceptibility map reconstruction., Journal of computer assisted tomography 36 : 265-274, 2012, 28 pages.
Chen et al., Susceptibility-based functional brain mapping by 3D deconvolution of an MR-phase activation map., J Neurosci Methods 216 : 33-42, 2013, 3 pages.
Chen et al., Nonlinear magnitude and linear phase behaviors of T2* imaging: theoretical approximation and Monte Carlo simulation., Magn Reson Imaging 33 : 390-400, 2015, 3 pages.
Chen et al., Intrinsic functional brain mapping in reconstructed 4D magnetic susceptibility (x) data space., J Neurosci Methods 241 : 85-93, 2015, 5 pages.
Chen et al., Task-evoked brain functional magnetic susceptibility mapping by independent component analysis (ICA), Journal of Neuroscience Methods 261 : 161-171, 2016, 3 pages.
Chen, Inverse Mapping of BOLD fMRI: 4D Magnetic Susceptibility (x) Tomography. In: (Ed.), Neuroimaging, SMGE Group, 2016, 16 pages.
Bianciardi et al., Investigation of BOLD fMRI resonance frequency shifts and quantitative susceptibility changes at 7T., Hum Brain Mapp 35 : 2191-2205, 2014, 24 pages.
Özbay et al., Probing neuronal activation by functional quantitative susceptibility mapping under a visual paradigm: A group level comparison with BOLD fMRI and PET, NeuroImage 137 : 52-60, 2016, 36 pages.
Mangia et al., Functional MRI with SWIFT, Proc. Intl. Soc. Mag. Reson. Med. 20 : 326, 2012, 1 page.
Lehto et al., Calcification Imaging with SWIFT in Rat Brain, Proc. Intl. Soc. Mag. Reson. Med. 19 : 700, 2011, 1 page.
Lehto et al., SWIFT Imaging of Myelin Loss in Traumatic Brain Injury in Rats, 20 : 917, 2012, 1 page.
Lehto et al., Detection of calcifications in vivo and ex vivo after brain injury in rat using SWIFT., Neuroimage 61 : 761-772, 2012, 23 pages.
Lehto et al., Phase Contrast of SWIFT in Rat Brain Ex Vivo, 20 : 2379, 2012, 1 page.
Lehto et al., Iron Imaging Using SWIFT in a Rat Model of Traumatic Brain Injury, 20 : 935, 2012, 1 page.
Lehto et al., Phase imaging in brain using SWIFT, Journal of Magnetic Resonance 252 : 20-28, 2015, 20 pages.

(56) References Cited

OTHER PUBLICATIONS

Corum et al,. Dipole Matched Filter with SWIFT, Proc. Intl. Soc. Mag. Reson. Med. 18 : 5113, 2010, 2 pages.
Corum et al., Dipole filtering, decomposition and quantification with 3D radial acquisition, Proc. Intl. Soc. Mag. Reson. Med. 23 : 1729, 2015, 1 page.
Menon, Postacquisition suppression of large-vessel BOLD signals in high-resolution fMRI., Magn Reson Med 47 : 1-9, 2002, 11 pages.
Rowe, Modeling both the magnitude and phase of complex-valued fMRI data., Neuroimage 25 : 1310-1324, 2005, 15 pages.
Rowe et al., Characterizing phase-only fMRI data with an angular regression model., J Neurosci Methods 161 : 331-341, 2007, 19 pages.
Sun et al., Structural and functional quantitative susceptibility mapping from standard fMRI studies., NMR in biomedicine, 2016, 2 pages.
Peters DC, Lederman RJ, Dick AJ, Raman VK, Guttman MA, Derbyshire JA, McVeigh ER. Undersampled projection reconstruction for active catheter imaging with adaptable temporal resolution and catheter-only views. Magn Reson Med. Feb. 2003;49(2):216-22. doi: 10.1002/mrm.10390. PMID: 12541240; PMCID: PMC2396305.
Barger AV, Block WF, Toropov Y, Grist TM, Mistretta CA. Time-resolved contrast-enhanced imaging with isotropic resolution and broad coverage using an undersampled 3D projection trajectory. Magn Reson Med. Aug. 2002;48 (2):297-305. doi: 10.1002/mrm. 10212. PMID: 12210938.
Pipe JG. Motion correction with Propeller MRI: application to head motion and free-breathing cardiac imaging. Magn Reson Med. Nov. 1999;42(5):963-9. doi: 10.1002/(sici)1522-2594(199911)42:5<963::aid-mrm17>3.0.co;2-l. PMID:10542356.
Schaäffter T, Rasche V, Carlsen IC. Motion compensated projection reconstruction. Magn Reson Med. May 1999;41(5):954-63. doi: 10.1002/(sici)1522-2594(199905)41:5<954::aid-mrm15>3.0.co;2-j. PMID: 10332879.
Pipe JG, Menon P. Sampling density compensation in MRI: rationale and an iterative numerical solution. Magn Reson Med. Jan. 1999;41(1):179-86. doi: 10.1002/(sici)1522-2594(199901)41:1<179::aid-mrm25>3.0.co;2-v. PMID 10025627.
Lauzon ML, Rutt BK. Polar sampling in k-space: reconstruction effects. Magn Reson Med. Nov. 1998;40(5):769-82. doi 10.1002/mrm.1910400519. PMID: 9797162.
Collins DL, Zijdenbos AP, Kollokian V, Sled JG, Kabani NJ, Holmes CJ, Evans AC. Design and construction of a realistic digital brain phantom. IEEE Trans Med Imaging. Jun. 1998;17(3):463-8. doi: 10.1109/42.712135. PMID: 9735909.
Boada FE, Gillen JS, Shen GX, Chang SY, Thulborn KR. Fast three dimensional sodium imaging. Magn Reson Med. May 1997;37(5):706-15. doi: 10.1002/mrm.1910370512. PMID: 9126944.
Lauzon ML, Rutt BK. Effects of polar sampling in k-space. Magn Reson Med. Dec. 1996;36(6):940-9. doi: 10.1002/mrm. 1910360617. PMID: 8946360.
Gai N, Axel L. Correction of motion artifacts in linogram and projection reconstruction MRI using geometry and consistency constraints. Med Phys. Feb. 1996;23(2):251-62. doi: 10.1118/1. 597713. PMID: 8668107.
Reeder SB, McVeigh ER. The effect of high performance gradients on fast gradient echo imaging. Magn Reson Med. Nov. 1994;32(5):612-21. doi: 10.1002/mrm.1910320510. PMID: 7808262; PMCID: PMC2396302.
Glover GH, Noll DC. Consistent projection reconstruction (CPR) techniques for MRI. Magn Reson Med. Mar. 1993;29(3):345-51. doi: 10.1002/mrm.1910290310. PMID: 8450743.
Glover GH, Pauly JM. Projection reconstruction techniques for reduction of motion effects in MRI Magn Reson Med. Dec. 1992;28(2):275-89. doi: 10.1002/mrm.1910280209 PMID: 1461126.
Jackson JI, Meyer CH, Nishimura DG, Macovski A. Selection of a convolution function for Fourier inversion using gridding [computerised tomography application], IEEE Trans Med Imaging. 1991;10(3):473-8. doi: 10.1109/42.97598. PMID:18222850.

Barrett HH. Objective assessment of image quality: effects of quantum noise and object variability. J Opt Soc Am A. Jul. 1990;7(7):1266-78. doi: 10.1364/josaa.7.001266. PMID: 2370589.
Duyn JH, van Gelderen P, Li TQ, de Zwart JA, Koretsky AP, Fukunaga M. High-field MRI of brain cortical substructure based on signal phase. Proc Natl Acad Sci U S A. Jul. 10, 2007;104(28):11796-801. doi: 10.1073/pnas.0610821104.Epub Jun. 22, 2007. PMID: 17586684; PMCID: PMC1913877.
Rauscher A, Sedlacik J, Barth M, Mentzel HJ, Reichenbach JR. Magnetic susceptibility-weighted MR phase imaging of the human brain AJNR Am J Neuraradiol. Apr. 2005;26(4):736-42. PMID: 15814914; PMCID: PMC7977092.
Mills PH, Wu YJ, Ho C, Ahrens ET. Sensitive and automated detection of iron-oxide-labeled cells using phase image cross-correlation analysis. Magn Reson Imaging. Jun. 2008;26(5):618-28. doi: 10.1016/j.mri.2008.01.007. Epub May 2, 2008. PMID: 18450402; PMCID: PMC3200563.
Baheza RA, Welch EB, Gochberg DF, Sanders M, Harvey S, Gore JC, Yankeelov IE. Detection of microcalcifications by characteristic magnetic susceptibility effects using MR phase image cross-correlation analysis. Med Phys. Mar. 2015;42(3):1436-52. doi: 10.1118/1.4908009. PMID: 25735297; PMCID: PMC4344475.
Haacke EM, Mittal S, Wu Z, Neelavalli J, Cheng YC. Susceptibility-weighted imaging: technical aspects and clinical applications, part 1. AJNR Am J Neuraradiol. Jan. 2009;30(1):19-30. doi: 10.3174/ajnr.A1400. Epub Nov. 27, 2008. PMID: 19039041; PMCID: PMC3805391.
Li H, Correa NM, Rodriguez PA, Calhoun VD, Adali T. Application of independent component analysis with adaptive density model to complex-valued fMRI data. IEEE Trans Biomed Eng. Oct. 2011;58(10):2794-803. doi: 10.1109/TBME.2011.2159841. Epub Jun. 16, 2011. PMID: 21690000; PMCID: PMC3179579.
Arbabshirani MR, Plis S, Sui J, Calhoun VD. Single subject prediction of brain disorders in neuroimaging: Promises and pitfalls. Neuroimage. Jan. 15, 2017;145(Pt B):137-165. doi: 10.1016/j.neuroimage.2016.02.079. Epub Mar. 21, 2016. PMID: 27012503; PMCID: PMC5031516.
Bridwell DA, Rachakonda S, Silva RF, Pearison GD, Calhoun VD. Spatiospectral Decomposition of Multi-subject EEG: Evaluating Blind Source Separation Algorithms on Real and Realistic Simulated Data. Brain Topogr. Jan. 2018;31 (1):47-61. doi: 10.1007/s10548-016-0479-1. Epub Feb. 24, 2016. PMID: 26909688; PMCID: PMC4996763.
Tang J, Liu S, Neelavalli J, Cheng YC, Buch S, Haacke EM. Improving susceptibility mapping using a threshold-based K-space/image domain iterative reconstruction approach. Magn Reson Med. May 2013;69(5):1396-407. doi: 10.1002/mrm.24384. Epub Jun. 26, 2012. PMID: 22736331; PMCID: PMC3482302.
Duyn J. MR susceptibility imaging. J Magn Reson. Apr. 2013;229:198-207. doi: 10.1016/j.jmr.2012.11.013. Epub Nov. 29, 2012. PMID: 23273840; PMCID: PMC3602381.
Yablonskiy DA, Haacke EM. Theory of NMR signal behavior in magnetically inhomogeneous tissues: the static dephasing regime. Magn Reson Med. Dec. 1994,32(6):749-63. doi: 10 1002/mrm. 1910320610 PMID: 7869897.
Fischl B, Wald LL. Phase maps reveal cortical architecture. Proc Natl Acad Sci U S A. Jul. 10, 2007;104(28):11513-4. doi: 10.1073/pnas.0704515104. Epub Jul. 3, 2007. PMID: 17609374; PMCID: PMC1913865.
Pathak AP, Ward BD, Schmainda KM. A novel technique for modeling susceptibility-based contrast mechanisms for arbitrary microvascular geometries: the finite perturber method. Neuroimage. Apr. 15, 2008;40(3): 1130-43. doi: 10.1016/.neuroimage.2008.01. 022. Epub Jan. 29, 2008. PMID: 18308587; PMCID: PMC2408763.
Chen Z, Caprihan A, Calhoun V. Effect of surrounding vasculature on intravoxel BOLD signal. Med Phys. Apr. 2010;37(4):1778-87. doi: 10.1118/1.3366251. PMID: 20443500; PMCID: PMC2864670.
He X, Yablonskiy DA. Biophysical mechanisms of phase contrast in gradient echo MRI. Proc Natl Acad Sci U S A. Aug. 11, 2009;106(32): 13558-63. doi: 10.1073/pnas.0904899106. Epub Jul. 23, 2009. PMID: 19628691; PMC2714760.
Feng Z, Caprihan A, Blagoev KB, Calhoun VD. Biophysical modeling of phase changes in BOLD fMRI. Neuroimage. Aug. 15,

(56) References Cited

OTHER PUBLICATIONS

2009;47(2):540-8. doi: 10.1016/j.neuroimage.2009.04.076. Epub May 5, 2009. PMID: 19426815; PMCID: PMC4336566.
Jensen JH, Chandra R, Ramani A, Lu H, Johnson G, Lee SP, Kaczynski K, Helpern JA. Magnetic field correlation imaging. Magn Reson Med. Jun. 2006;55(6):1350-61. doi: 10.1002/mrm. 20907. PMID: 16700026.
Jenkinson M, Wilson JL, Jezzard P. Perturbation method for magnetic field calculations of nonconductive objects. Magn Reson Med. Sep. 2004;52(3):471-7. doi: 10.1002/mrm.20194. PMID: 15334564.
Li L, Leigh JS. Quantifying arbitrary magnetic susceptibility distributions with MR. Magn Reson Med. May 2004;51(5):1077-82. doi: 10.1002/mrm.20054. PMID: 15122694.
Boxerman JL, Hamberg LM, Rosen BR, Weisskoff RM. MR contrast due to intravascular magnetic susceptibility perturbations. Magn Reson Med. Oct. 1995;34(4):555-66. doi: 10 1002/mrm 1910340412 PMID: 8524024.
Kennan RP, Zhong J, Gore JC. Intravascular susceptibility contrast mechanisms in tissues. Magn Reson Med. Jan. 1994;31(1):9-21.doi: 10.1002/mrm. 1910310103. PMID: 8121277.
Ogawa S, Lee TM. Magnetic resonance imaging of blood vessels at high fields: in vivo and in vitro measurements and image simulation. Magn Reson Med. Oct. 1990;16(1):9-18. doi: 10.1002/mrm. 1910160103. PMID: 2255240.
Ogawa S, Lee TM, Kay AR, Tank DW. Brain magnetic resonance imaging with contrast dependent on blood oxygenation. Proc Natl Acad Sci U S A. Dec. 1990;87(24):9868-72. doi: 10.1073/pnas.87. 24.9868. PMID: 2124706; PMCID: PMC55275.
Kwong KK, Belliveau JW, Chesler DA, Goldberg IE, Weisskoff RM, Poncelet BP, Kennedy DN, Hoppel BE, Cohen MS, Turner R, et al. Dynamic magnetic resonance imaging of human brain activity during primary sensory stimulation. Proc Natl Acad Sci U S A. Jun. 15, 1992;89(12):5675-9. doi: 10.1073/pnas.89.12.5675. PMID: 1608978; PMCID: PMC49355.
Liu C, Li W. Imaging neural architecture of the brain based on its multipole magnetic response. Neuroimage. Feb. 13, 2013;67:193-202 doi: 10.1016/j.neuroimage.2012.10.050. Epub Oct. 29, 2012. PMID: 23116817; PMCID: PMC3640835.
Li J, Chang S, Liu T, Wang Q, Cui D, Chen X, Jin M, Wang B, Pei M, Wisnieff C, Spincemaille P, Zhang M, Wang Y. Reducing the object orientation dependence of susceptibility effects in gradient echo MRI through quantitative susceptibility mapping. Magn Reson Med. Nov. 2012;68(5): 1563-9. doi: 10.1002/mrm.24135. Epub Jan. 3, 2012. PMID: 22851199; PMCID: PMC3493252.
Liu C, Wei H, Gong NJ, Cronin M, Dibb R, Decker K. Quantitative Susceptibility Mapping: Contrast Mechanisms and Clinical Applications. Tomography. Sep. 2015;1(1):3-17. doi: 10.18383/j.tom. 2015.00136. PMID: 26844301; PMCID: PMC4734903.
Poynton CB, Jenkinson M, Adalsteinsson E, Sullivan EV, Pfefferbaum A, Wells W 3rd. Quantitative susceptibility mapping by inversion of a perturbation field model: correlation with brain iron in normal aging. IEEE Trans Med Imaging. Jan. 2015;34(1):339-53. doi: 10.1109/TMI.2014.2358552. Epub Sep. 1, 20146. PMID: 25248179; PMCID: PMC4404631.
McKee et al.,"A Simple Technique for Encapsulating NMR Coils in Teflon PTFE," Journal of Physics E: Scientific Instruments, vol. 9, No. 10, pp. 3 (1976).
Haacke et al., "Susceptibility weighted imaging (SWI)," Magnetic resonance in medicine, Vo . 52, Issue 3: pp. 612-618, 11 pages total (2004).
The International Search Report and Written Opinion for International Application No. PCT/US2018/059582 dated Feb. 14, 2019 (8 pages).
Feng et al., XD-GRASP: Golden-Angle Radial MRI with Reconstruction of Extra Motion-State Dimensions Using Compressed Sensing, Magn Reson Med., Feb. 2016., 75(2) 25 pages.
Zaitsev et al., Motion Artifacts in MRI: A Complex Problem with Many Partial Solutions, J Magn Reson Imaging, Oct. 2015., 42(4), 30 pages.
Corum et al., High-Spatial- and High-Temporal-Resolution Dynamic Contrast-enhanced MR Breast Imaging with Sweep Imaging with Fourier Transformation: A Pilot Study, Radiology, Feb. 2015., 274(2), 8 pages.
Samsonov, Alexey, Adaptive retrospective correction of motion artifacts in cranial MRI with multicoil three-dimensional radial acquisitions, Magn Reson Med., Apr. 2013., 69(4), 22 pages.
Cheng et al., Nonrigid Motion Correction in 3D Using Autofocusing with Localized Linear Translations, Magn Reson Med., Dec. 2012., 68(6) 27 pages.
Hansen et al., Retrospective Reconstruction of High Temporal Resolution Cine Images from Real-Time MRI Using Iterative Motion Correction, Magn Reson Med., Sep. 2012., 68(3) 18 pages.
Lin et al., High Temporal Resolution Retrospective Motion Correction with Radial Parallel Imaging, Magn Reson Med., Apr. 2012., 67(4), pp. 1097-1105.
Bhat et al., 3D Radial Sampling and 3D Affine Transform-based Respiratory Motion Correction Technique for Free-Breathing Whole-Heart Coronary MRA with 100% Imaging Efficiency, Magn Reson Med., May 2011, 65(5), 17 pages.
Samsonov et al., POCS-enhanced correction of motion artifacts in parallel MRI, Magn Reson Med., Apr. 2010, 63(4) 16 pages.
Brodsky et al., Characterizing and Correcting Gradient Errors in Non-Cartesian Imaging: Are Gradient Errors Linear Time-Invariant (LTI)?, Magn Reson Med., Dec. 2009., 62(6), 1466-1476 pages.
Roy et al., On the Regulation of the Blood-Supply of the Brain., J Physiol., Jan 1890. 11(1-2):85-158.17. doi: 10.1113/physiol.1890. sp000321. PMID: 16991945; PMCID: PMC1514242.
Ogawa et al, ,Oxygenation-Sensitive Contrast in Magnetic Resonance Image of Rodent Brain at High Magnetic Fields., Magn Reson Med, 14, pp. 68-78, (1990).
Ogawa et al., Intrinsic Signal Changes Accompanying Sensory Stimulation: Functional Brain Mapping with Magnetic Resonance Imaging., Proc. Natl. Acad. Sci USA, vol. 89, pp. 5951-5955, (1992).
Buxton, Richard B., The physics of functional magnetic resonance imaging (fMRI), Rep Prog Phys., Sep. 2013., 76(9), 55 pages.
Hillman, Elizabeth M.C., Coupling Mechanism and Significance of the BOLD Signal: A Status Report, Ann Rev of Neurosci., Jul. 8, 2014, 37, pp. 161-181.
Arbabshirani et al., Single Subject Prediction of Brain Disorders in Neuroimaging: Promises and Pitfalls, NeuroImage, vol. 145, Part B, Jan. 15, 2017, 77 pages.
Dubois et al,. Building a Science of Individual Differences from fMRI., Trends in Cognitive Sciences, Cell Press, pp. 1-19, (2016).
Shah et al., Reliability and reproducibility of individual differences in functional connectivity acquired during task and resting state, Brain and Behavior 6(5), 2016, 15 pages.

\* cited by examiner

FUNCTIONAL MAGNETIC RESONANCE IMAGING WITH DIRECT DIPOLE DECOMPOSITION

CROSS-REFERENCE TO RELATED APPLICATIONS

This application claims the benefit of PCT Application No. PCT/US2018/059582, filed Nov. 7, 2018, entitled "Functional Magnetic Resonance Imaging With Direct Dipole Decomposition" and U.S. Provisional Patent Application No. 62/582,356, filed on Nov. 7, 2017 and entitled "Next Generation Functional Imaging", both of which are incorporated herein by reference.

BACKGROUND

Typically, functional imaging is carried out by one of two main methods. Nuclear Medicine methods such as positron emission tomography (PET) and single photon emission computed topography (SPECT), and blood oxygen level dependent (BOLD) functional magnetic resonance imaging (fMRI). By far the most commonly used method, for both research studies and clinical applications, is fMRI.

BOLD fMRI is possible due to the BOLD effect, blood oxygen level dependent, discovered in the early 1990s. While the physiology of the BOLD mechanism is still not fully understood the main theory is as follows. Neuronal activity, such as the generation of action potentials in neurons and synaptic transmission requires increased metabolic activity for the neurons involved. A signaling mechanism triggers the hemodynamic response (HR), increasing blood flow to the active brain region. With increased blood flow, the oxygenation state of the hemoglobin is more saturated. Since oxyhemoglobin is diamagnetic and not paramagnetic, an increase in the signal results in the active brain region when using a $T_2$*weighted MRI sequence.

Non-invasive functional neuroimaging, first with PET and subsequently with BOLD fMRI, has led to a revolution in understanding of the brain. Basic neuroscience, psychology, psychiatry, neurology, as well as numerous other fields routinely utilize fMRI to study the "resting" and "active" human brain. In particular, independent component analysis (ICA) of resting-state fMRI (rsfMRI) datasets has grown into a ubiquitous research tool, which potentially holds great diagnostic value should it become powerful enough to classify or differentiate at an individual patient and subject level.

Within the first decade of fMRI research, the potential for multi-site studies was already recognized and investigated. Numerous fMRI research studies and multi-center clinical trials have been completed, virtually all utilizing fMRI as an indicator or outcome at a group level. Yet after nearly three decades of fMRI research and some clinical translation, fMRI has progressed much slower than other MRI methods in providing diagnostic information for individual research subjects and patients. Single or multi-center trials correlating fMRI biomarkers to individual patient intervention or pathology are still highly problematic.

There are two fundamental limitations that need to be overcome in order to improve fMRI as a research tool or achieve diagnostic significance for individual patients: The first fundamental limitation is the physiological noise, which includes gross and physiological motion, temporal aliasing of rapid processes, blood flow and interaction by activation in nearby or distant voxels.

The second fundamental limitation is the instrumental noise, which depends on the exact experimental equipment, paradigms and parameters, including their interaction with hard-to-control nuisance parameters such as motion. Currently, it is not possible to isolate the variability of the underlying experimental data from the variability of the protocols and analysis methods. The general difficulty and even "unreliability" of some fMRI studies is of increasing concern to the research community.

The effort to supply standard protocols on proven hardware to multiple sites (maximizing the similarities of as many parameters as possible) is a necessary and worthy approach. Yet, protocols still have the fundamental limitations of sensitivity to nuisance parameters, physiological and instrumental noise.

ICA and related methods applied to echo planar imaging (EPI) time series have shown potential to disentangle physiological noise from actual brain activity. ICA also has the potential to take advantage of external motion tracking and physiological monitoring systems. However, it is still challenging to create fMRI acquisition and ICA analysis protocols that allow a reliable extraction of the components.

Until more robust combined acquisition and analysis methods are developed (which greatly reduce instrumental and physiological noise sensitivity), fMRI will continue to be plagued by lack of comparability between datasets and will face limitations in statistical power, even for large enrollments.

Phase or Field-based BOLD (pBOLD) detection is a promising method to significantly reduce physiological and instrumental noise. The pBOLD fMRI takes advantage of the linearity of the MRI signal at shorter echo times to detect BOLD-based local spin frequency as a change in the phase in the reconstructed magnetic resonance image rather than magnitude changes. Current pBOLD fMRI techniques, such as, functional quantitative susceptibility mapping (fQSM) hold great potential, but are in an early stage of investigation.

One critical problem is the current workhorse of fMRI, echo planar imaging (EPI). While considered essential in order to freeze gross motion and acquire rapid time series data, EPI suffers from phase instability from eddy currents, gradient non-idealities and fluctuations, and sequence timing errors. EPI is fundamentally limited by phase instabilities and yields a poor noise floor for phase images.

Most other standard MRI sequences such as two-dimensional (2D) or three-dimensional (3D) spoiled gradient echo (e.g., fast low angle shot, spoiled gradient echo (FLASH)) are not suitable for practical pBOLD fMRI either. As a rule of thumb, the more acoustic noise the sequence makes, the more eddy currents, gradient errors and related phase noise are created.

For these and other reasons, there is a need for the present disclosure.

SUMMARY

Some embodiments of the present disclosure relate to a system. The system includes a machine readable storage medium storing instructions and a processor to execute the instructions. The processor executes the instructions to receive radial k-space magnetic resonance imaging (MRI) data of a patient and determine a series of dipole sources via direct dipole decomposition of the radial k-space MRI data. The processor executes the instructions to identify an activation within the patient based on the series of dipole sources.

Yet other embodiments of the present disclosure relate to a system. The system includes a machine readable storage medium storing instructions and a processor to execute the instructions. The processor executes the instructions to receive radial k-space magnetic resonance imaging (MRI) data of a patient. The processor executes the instructions to generate a first subset of the radial k-space MRI data for a first time and generate a second subset of the radial k-space MRI data for a second time. The processor executes the instructions to determine a first series of dipole sources via direct dipole decomposition of the first subset and determine a second series of dipole sources via direct dipole decomposition of the second subset. The processor executes the instructions to detect movement of the patient based on the first series of dipole sources and the second series of dipole sources.

Yet other embodiments of the present disclosure relate to a coil for a magnetic resonance imaging (MRI) system. The coil includes a transmit coil, a receiver coil, and a proton free polymer (e.g., PTFE, PCTFE) housing enclosing the transmit coil and the receiver coil.

Additional features and advantages will be set forth in the detailed description which follows, and in part will be readily apparent to those skilled in the art from that description or recognized by practicing the embodiments as described herein, including the detailed description which follows, the claims, as well as the appended drawings. It is to be understood that both the foregoing general description and the following detailed description are merely exemplary, and are intended to provide an overview or framework to understanding the nature and character of the claims.

DETAILED DESCRIPTION

Figure 1:
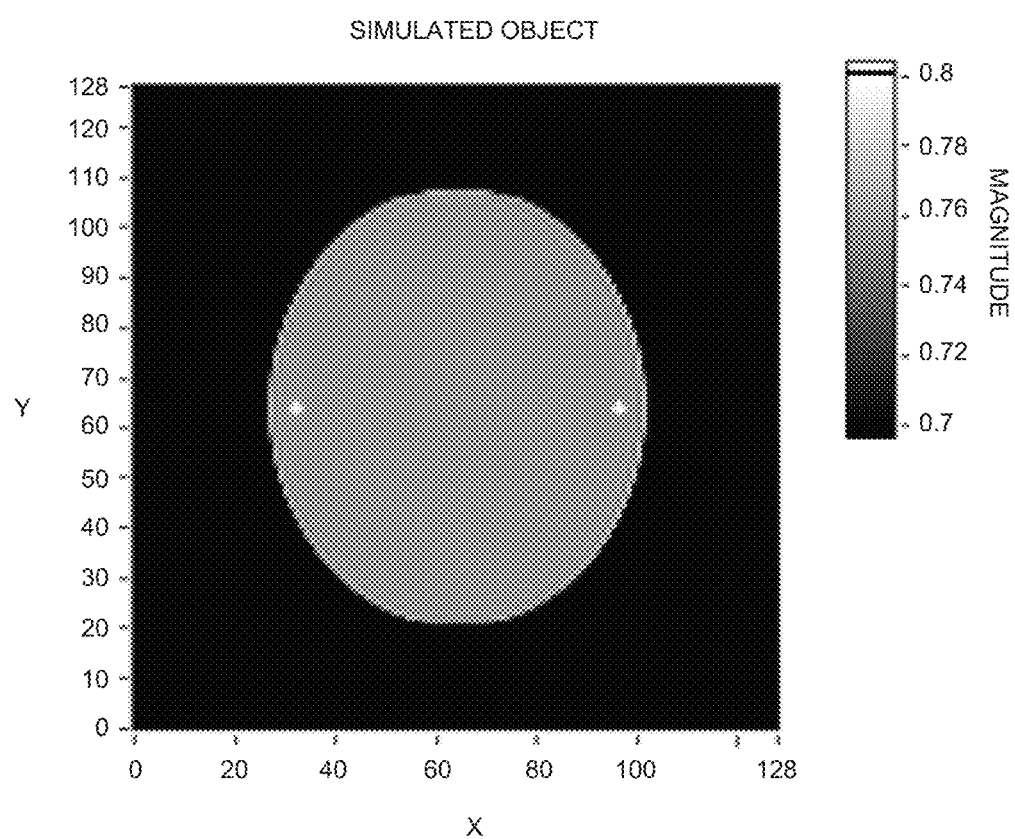
FIG. 1 illustrates one example of the magnitude of a simulated object representing a transverse head slice.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

As used herein, the following acronyms, abbreviations, notations and definitions are defined as follows:
PET: positron emission tomography
SPECT: single photon emission computed topography
BOLD: blood oxygen level dependent
fMRI: functional magnetic resonance imaging
HR: hemodynamic response
$T_2^*$: apparent transverse relaxation time
$T_2$: transverse relaxation time
MRI: magnetic resonance imaging
ICA: independent component analysis
rsfMRI: resting-state fMRI
EPI: echo planar imaging
pBOLD: Phase or Field-based BOLD
QSM: quantitative susceptibility mapping
fQSM: functional quantitative susceptibility mapping
1D: one-dimensional
2D: two-dimensional
3D: three-dimensional
FLASH: fast low angle shot, spoiled gradient echo
SWI: susceptibility weighted imaging
CI-fMRI: computed image fMRI
FID: free induction decay
TE: echo time
SWIFT: sweep imaging with Fourier transformation
RUFIS: rotating ultra-fast imaging sequence
ZTE: zero TE
RF: radiofrequency
ms: millisecond
k-space: Fourier domain data in MRI.
3 T: 3 Tesla, field strength of MRI scanner.
T/R: transmit receive
coil: apparatus for transmitting and receiving RF frequency electromagnetic fields for MRI.
ringdown: decay of stored (resonant) RF frequency energy from a coil.

DDD: direct dipole decomposition

SVD: singular value decomposition

MEG: Magnetoencephalography magnetization preparation: section of the MRI pulse sequence that creates a specific contrast state, usually encoded in the longitudinal magnetization.

sequence: abbreviated form of "pulse sequence", the series of RF and gradient waveforms produced by the MRI scanner.

magnitude: the magnitude of the complex k-space data or reconstructed image data.

phase: the phase of the complex k-space data or reconstructed image data.

phase noise: noise in the phase component of k-space or image data. Can be caused by disturbances to the quasistatic magnetic field by patient motion, physiological motion, eddy currents and sequence timing errors.

radial: MRI acquisition in which k-space is sampled by a series of lines originating at the origin (for FID) sequences or passing through (for gradient echo or spin echo sequences). Can be two or three dimensional.

FOV: Field of View. The volume captured by the pulse sequence and coil combination.

field: abbreviated form of magnetic field.

isocenter: the common center of the main magnet and each of the gradient and shim coils in an MRI scanner.

shim coil: electromagnet wound to produce a small magnetic field in order to compensate for susceptibility induced variation (inhomogeneities) from the patient or object placed in the MRI scanner and also from residual imperfections to the main magnet.

spherical harmonic: function describing the spatial magnetic field strength of a shim coil. A mathematically known orthogonal set of functions.

field inhomogeneities: spatial variations in the magnetic field.

decomposing: partitioning numerical data into a set of coefficients and basis functions which (at least approximately) represents the original data. i.e. fourier decomposition, spherical harmonic decomposition, dipole decomposition.

Source: a (small) volume of the object (patient) that produces a magnetic field a distance away from itself. The actual volume of the source may or may not produce MRI observable signal but the source coordinates can be determined by the magnetic field produced in nearby or more distant MRI observable volumes.

Disclosed herein are systems and methods using direct dipole decomposition to detect and quantify BOLD activation by fitting a basis of time-varying secular dipoles directly to the raw data without the intermediate step of phase and/or magnitude image reconstruction. In DDD, reconstruction of a full image before determining activation is not performed or desired. Functional activation is extracted directly from the raw acquired data without confound from image artifacts. In addition, rigid and higher order motion is captured and corrected (by tracking of anatomical dipoles of the sinuses, ear canals, skull, vasculature and other sharp susceptibility features) at the level of individual projections.

The systems and methods described herein provide for greatly improved quantitative phase and field imaging especially suitable for functional magnetic resonance imaging (fMRI) with significance at the level of an individual patient or research subject. The functional imaging described herein provides dramatically reduced physiological and instrumental noise, and mitigates or eliminates confounds of auditory, vibration, and gradient stimulation.

In one example of the present disclosure, MRI is performed with direct dipole decomposition and "list mode" processing. List mode, when combined with direct dipole decomposition allows the spatiotemporal field components due to the BOLD effect to be carried out directly (without image reconstruction) on a "flattened list" of 1D projections versus time, a computationally simple and efficient operation.

In a second example of the present disclosure, motion of the patient is tracked and corrected by detecting areas of strong susceptibility as a magnetic dipole by direct dipole decomposition before subsequent direct dipole decomposition for time series of fMRI activation as well as high resolution anatomical image reconstruction.

Phase/Field-based MRI may directly capture dipole magnetic fields generated from neural activity, simultaneous with BOLD, if temporal sampling are increased and field/phase noise is significantly reduced. Other features can also be captured, such as static susceptibility changes from normal (tissue interfaces) and abnormal (scarring, microbleeds and clots, calcifications, tumors) tissues as well as foreign bodies.

An advantage of phase/field based MRI for BOLD fMRI, which is called pBOLD fMRI herein, is that BOLD activation is captured as a physically meaningful parameter, the change in magnetic field from change in secular dipole moment in the voxel. This change is also proportional to field strength for the foreseeable range of MRI scanner field strengths. The above is in contrast to current BOLD fMRI based on magnitude changes at longer echo times. The nonlinear dependence on numerous uncontrolled parameters is the source of difficulty in harmonizing results between multiple sites, field strengths, protocols, and vendor platforms.

There are two major stumbling blocks for practical phase based bold, one is phase noise in the raw data, the other phase artifacts in reconstructed images.

FID acquisition—A FID (free induction decay) acquisition sequence provides a rapid acquisition method with stable and minimal phase noise baseline. FID acquisition sequences (SWIFT and ZTE/RUFIS) have already been utilized for fMRI in early proof of principle fMRI studies. The BOLD contrast mechanism was either dominated by inflow or utilized a $T_2^*$preparation to yield magnitude BOLD changes. FID imaging is utilized herein to obtain reliable phase-based BOLD (pBOLD) contrast. FID acquisition sequences reduce the crippling eddy currents that have hampered pBOLD efforts to date, and also reduce acoustic noise, vibration, and unintended neurostimulation due to drastically reducing gradient slew rates.

Zero echo time (ZTE)—The zero echo time (ZTE) sequence, although not named at the time, was the first MRI method, used by Lauturbur which utilized hard pulse excitation in a gradient and FID acquisition. It was subsequently re-discovered after Cartesian phase encode echo-based sequences became the norm for MRI.

SWeep Imaging with Fourier Transformation (SWIFT)—is an emerging zero echo time based MRI technique that is being investigated for use in an increasing number of applications. Unlike conventional MRI, in which excitation by a radiofrequency (RF) pulse and acquisition of the signal are separated by an echo time (TE) of 1 ms or longer, SWIFT utilizes nearly simultaneous time-interleaved sweep excitation and acquisition. Since excitation, frequency encoding, and acquisition are all simultaneous, SWIFT utilizes 3D radial k-space sampling where the orientation of the readout gradient is updated in small increments instead of being pulsed on and off or reversed. This leads to very low sound pressure level and minimal eddy currents. These characteristics make SWIFT ideal for imaging objects with extremely fast effective transverse relaxation times ($T_2$) and reduce sensitivity to subject motion while minimizing signal dropout due to field inhomogeneities. SWIFT's principal advantages over other zero echo time techniques are its ability to achieve higher flip angles and its extreme efficiency (nearly always acquiring) due to minimal gradient spoiling or ramping time.

Other radial sequences such as radial gradient echo, radial spin echo, radial multiple echo and hybrid (radial GRASE) may also be used but lack the timing error immunity and low field disturbance of FID sequences.

Maximal Dampening for Transmit-Only/Receive-Only Coils—There are many commercially available head coils on the market for 3T, but none of these are capable of FID acquisition sequences, primarily due to long ringdown times. Previous attempts for maximal dampening to reduce the recovery time in coils have been limited to single channel transmit/receive coils.

FID Acquisition Coil Housing—The second problem for commercially available head coils is that the housing materials produce visible signals, often generating artifacts in the image. Low proton background materials and production processes are needed to optimize materials for both FID acquisition sequence and for clinical safety.

Zero Echo Time Acquisition Coils—Combining the two previous innovations (maximal dampening for transmit-only, receive-only coils with zero echo time acquisition coil housing) provides a new generation of coil design that allows for current clinical pulse sequences as well as new FID acquisition sequences.

Direct Digitization on the Coil—Current OEM receiver chains are not sufficiently robust for FID acquisition sequences. Therefore, software-defined radio modules are disclosed herein to meet the fast data processing requirement of FID acquisition sequences. Direct digitization may be accomplished at the coil.

Phase images are more vulnerable to under-sampling artifacts. Avoiding image reconstruction altogether and estimating static and time varying phase changes via model based estimation may be preferable.

Direct Dipole Decomposition (DDD)—Reconstructing a QSM or fQSM image is a fundamentally ill-posed inversion process as commonly formulated. One method to obtain useful information from ill posed inverse problems is to limit the amount of information one wishes to obtain. Tikonov regularization and the Truncated SVD are two relatively well known algorithms which have been investigated as elements of fast QSM image reconstruction. Best is when full inversion or reconstruction does not take place and parameters can be directly estimated using orthogonal projection operators. Prior or joint reconstruction of the (ill posed) susceptibility image (and associated time/complexity) becomes an unnecessary bottleneck for obtaining the pBOLD activation.

Finite Secular Dipole Basis for pBOLD—A "secular dipole field" is the component of a dipole's field parallel to the direction of a much larger magnetic field, as is the case of susceptibility changes in tissue superimposed on the much larger $B_0$ field in MRI. The conceptual framework of the secular dipole matched filter and the signal equation for the field effects of point dipole sources on SWIFT/ZTE MRI phase images to model and estimate the frequency offsets due to pBOLD activated brain regions using a basis of temporally varying dipole sources has been extended herein.

The simplifying concept of finding pBOLD activation as a finite list of temporally varying secular dipole sources has not been utilized until now. The concept of decomposing pBOLD activation as a set of temporally varying secular magnetic dipole sources is similar in concept to Magnetoencephalography (MEG) except that the sources are secular and not due to direct neural currents, but due to local susceptibility fields from pBOLD.

3D Radial MRI as the natural coordinate system for finding dipoles—The secular dipole basis for pBOLD and other susceptibility sources is most naturally formulated in spherical coordinates. The natural sampling geometry is then spherical as well, corresponding to 3D Radial MRI. In addition, a basis of higher order spherical harmonic functions becomes computationally simple to utilize.

Direct Dipole Decomposition (DDD): DDD utilizes an estimated table of secular dipoles as the model the phase of projection data or the differences between subsequent views (taken at differing times) at the same polar angle.

DDD is a model based parameter estimation of the phase image or more conveniently, the phase of the 3D radial views (raw data). The model consists of time varying amplitudes of secular dipoles and their locations (which are assumed to be fixed with a small residual after motion correction). In DDD the off-resonance phase between sets of views is decomposed into a table (sum) of sources which best account for the total image (or viewset) phase with a small residual error term:

$$\Delta B(\vec{r}, t) = \sum_N \Delta B_n(\vec{r}, t) + \Delta B_{res}(\vec{r}, t).$$

Each table entry is a secular dipole$^{d_n(t)}$ creating a magnetic field profile:

$$\Delta B_n(\vec{r}, t) = \frac{-3\mu_0}{4\pi} d_n(t) \frac{\Lambda(\vec{r_n'})}{|\vec{r} - \vec{r_n'}|} \text{ where } \Lambda(\vec{r}) \equiv \frac{3(\hat{r} \cdot \hat{z})^2 - 1}{2}.$$

Magnitude changes (contrast injection or inflow) do not change the dipole moment unless there is an associated susceptibility change. Also, secular dipoles form orthogonal basis allowing the use of efficient and stable algorithms. After the complex subtraction of the phase information of the projection data between subsequent views at the same polar angle, a modified phase based dipole matched filter is used to estimate strong dipole sources in the field of view and then a model-based dipole-source decomposition 3D radial sampled data. Due to the spherical polar symmetry of the secular dipole field, the dipole source decomposition is most conveniently carried out using decimated radial k-space (3d→1d projection) data before image reconstruction. The dipole decomposition provides information allowing field estimation as well as generating the dipole activation map.

The signal equation and direct dipole decomposition (DDD) equation follow. The signal $\tilde{S}(\vec{k})$ for ZTE or SWIFT after correlation is given by Equation 1. For simplicity it is assumed to be a single channel with uniform response over volume V, but can be for each channel when the sensitivity of the coil channel is included.

$$\tilde{S}(\vec{k}) = \int_V \tilde{S}(\vec{r}) e^{-i2\pi \vec{r} \cdot \vec{k}} d^3r \quad \text{Equation 1}$$

where $\tilde{S}(\vec{r})=\tilde{S}(\vec{r})e^{i\phi}$ and $\phi=\gamma\Delta B(\vec{r})t$, where $\Delta B(\vec{r})$ is the spatial change in the local magnetic field, and t is the time since excitation. When $\beta\Delta Bt \ll 1$ then $e^{i\beta\Delta Bt} \approx 1+i\gamma\Delta Bt$ and:

$$\tilde{S}(\vec{k})=\int_{\vec{r}} S(\vec{r})e^{-i\pi \vec{r}\cdot\vec{k}}d^3r + i\int_{\vec{r}} S(\vec{r})[\gamma\Delta B(\vec{r})t]e^{-i2\pi \vec{r}\cdot\vec{k}}d^3r \quad \text{Equation 2}$$

with the first term on the right originating from the real valued magnitude in object space and the second the imaginary off resonance signal in object space. For ZTE/SWIFT the k-space trajectory is center out $\vec{k}=\gamma\vec{g}t$. Let the field change be due to a single secular dipole $\Delta B=d$ located at position $\vec{r}_o$ and carry out the Fourier transform for d:

$$\tilde{S}(\vec{k}) = S(\vec{k}) + i\left[S(\vec{k}) * d(\vec{k})\right]\frac{k}{g} \quad \text{Equation 3}$$

where $$d(\vec{k}) \equiv d_0 \Lambda(\theta) e^{-i2\pi \vec{r}_0 \cdot \vec{k}},$$

$$\Lambda(\theta) = \frac{3\cos^2(\theta) - 1}{2}$$

and $\theta=\hat{k}\cdot\hat{z}$. The convolution can be evaluated with the approximation $\tilde{S}(\vec{k}) \approx S_0 \delta(\vec{k})$ which means replacing $S(\vec{k})$ by its value at the center of k-space. Therefore:

$$\tilde{S}(\vec{k}) = S(\vec{k}) + iS_0 \frac{k}{g} d_0 \Lambda(\theta) e^{-i2\pi \vec{r}_0 \cdot \vec{k}} \quad \text{Equation 4}$$

To recover the dipole location and moment (Direct Dipole Decomposition, DDD) a normalized projection operation is performed on the k-space data:

$$d_0 = \tilde{S}(\vec{k}) \frac{g}{k} \left[\frac{e^{-i2\pi \vec{r}_0 \cdot \vec{k}}}{iS_0 \Lambda(\theta)}\right] \quad \text{Equation 5}$$

noting that $$S(\vec{k}) \frac{g}{k} \frac{e^{-i2\pi \vec{r}_0 \cdot \vec{k}}}{iS_0 \Lambda(\theta)} = 0.$$

The operation in Equation 5 is repeated to find all dipole sources in the k-space data. The operation in Equation 5 can be done on a small set of projections. It is assumed that the number of dipoles that can be recovered in a dataset is a small integer fraction times the number of projections available.

Direct to ICA and List mode processing—DDD combined with the idea of "list mode" processing, introduced originally for SPECT and PET, allows the ICA analysis using the secular dipole basis to be carried out directly on "flattened list" of 1D projections versus time, a computationally simple and efficient operation.

Motion Correction:

Large static dipole fields naturally occur at the sinus and ear canal interfaces; using these as fiducial markers, motion tracking and correction is applied to the raw data. For example, see FIGS. 1 and 4.

Motion correction and complex subtraction of motion-corrected views removes the object-dependent background signal.

Dipole Motion Tracking—Self-navigated motion tracking has been achieved for a number of MRI applications using 3D radial imaging. Some general MRI motion tracking methods can successfully utilize low resolution "keyhole" images, reduced dimensionality navigators, or other simplified estimates. Often the methods are confounded by susceptibility or other artifacts. Since zero echo time sequences such as SWIFT and ZTE do not lose signal due to areas of strong susceptibility, such areas can be thought of as "built-in fiducials" or "intrinsic markers" and detected as a magnetic dipole. Such areas usually correspond to the highest amplitude dipoles in the data.

Field Estimation:

Using the Field correction information, the user can either reacquire the data, utilize for real time shim update or apply field corrections for image reconstruction.

Field estimation is similar to the Direct Dipole Decomposition described above except that the basis is real-valued zonal and tesseral spherical harmonics up to a fixed order and only the relative strengths of each component, not the location of the center is estimated. Each component is centered at isocenter.

The spherical harmonic basis is typically limited to an order up to that of the electromagnetic shim coils installed or to that practical for post processing correction of k-space data (l=2 or 3, m=−l to l).

Dipole Activation Map:

is a phase image showing the activated dipoles fields. See for example, FIGS. 2 and 5.

ICA Spatiotemporal Filtering:

The preliminary dipole activation map can further be processed as constrained spatiotemporal components. In this disclosure, the components consist of candidate time varying dipoles, and are fitted to motion corrected projection data rather than reconstructed phase images. The approach is also known as model based parameter estimation and mitigates or eliminates confounds from under-sampling and image domain artifacts.

Motion Corrected High Spatial Resolution MP Imaging:

The anatomical reference image is reconstructed from motion and field corrected data.

FIG. 1 illustrates one example of the magnitude of a simulated object representing a transverse head slice. The x-axis and the y-axis are in units of voxel index (2 mm voxels). Two 250 Hz dipoles roughly corresponding to the ear canals and three 10 Hz dipoles corresponding to activation in the visual cortex V1 are included in the simulation. The 250 Hz dipoles are visible in the magnitude image which has bandwidth of 500 Hz/pixel. The 10 Hz dipoles are not visible.

Figure 2:
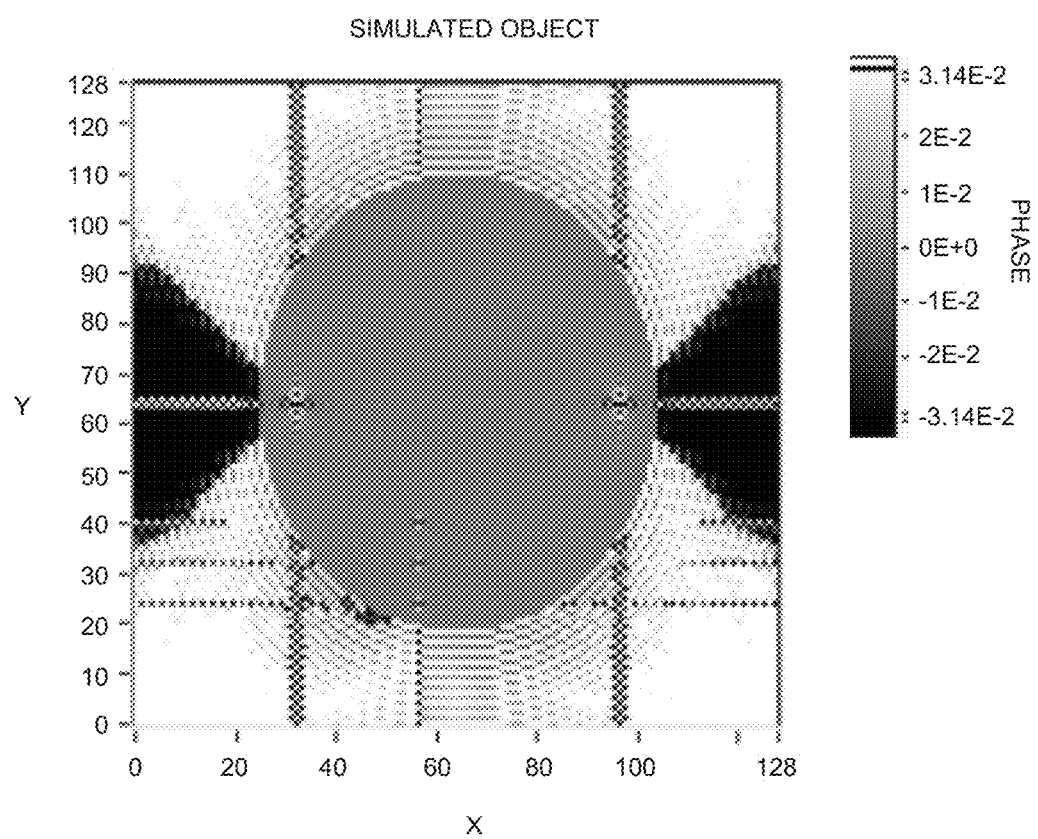
FIG. 2 illustrates one example of the phase of the simulated object of FIG. 1.

FIG. 2 illustrates one example of the phase of the simulated object, mainly due to the dipoles. The x-axis and the y-axis are in units of voxel index (2 mm voxels). The 10 Hz dipoles are visible at the scale shown.

Figure 3:
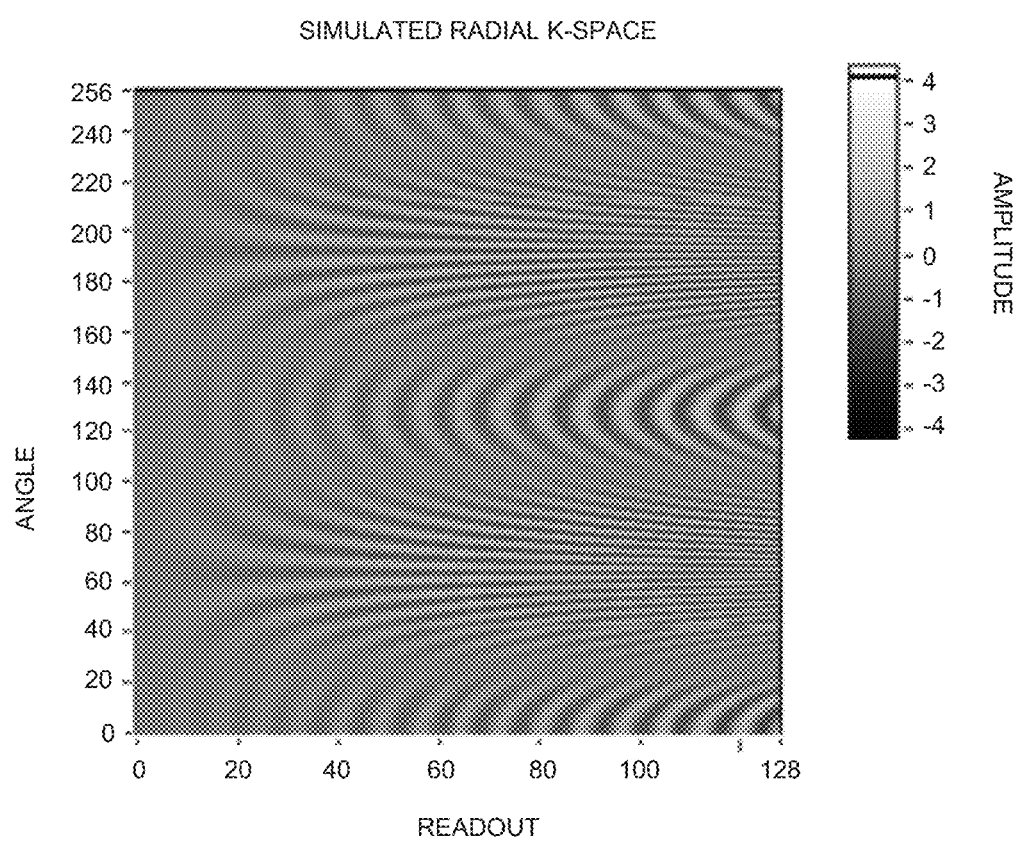
FIG. 3 illustrates one example of simulated radial k-space data.

FIG. 3 illustrates one example of simulated radial k-space data. The x-axis is the index of the readout and the y-axis is the angle in degrees. The imaginary component is shown, corresponding mainly to the effects of the dipoles.

Figure 4:
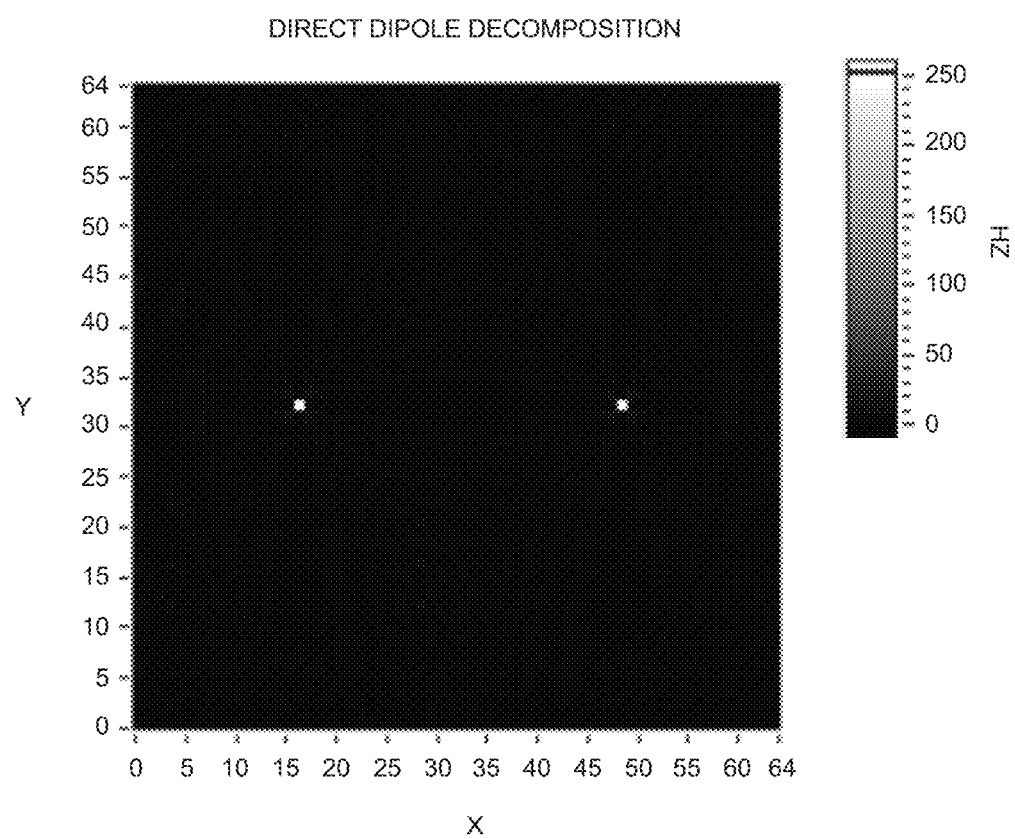
FIG. 4 illustrates one example of the results of direct dipole decomposition on the radial views.

FIG. 4 illustrates one example of the results of direct dipole decomposition on the radial views. The x-axis and the y-axis are in units of voxel index (4 mm voxels). The direct dipole decomposition has been applied to both the real and imaginary components of the radial k-space data. At the scale shown, the two 250 Hz dipoles (with amplitude determined from the calibrated decomposition) are clearly visible.

Figure 5:
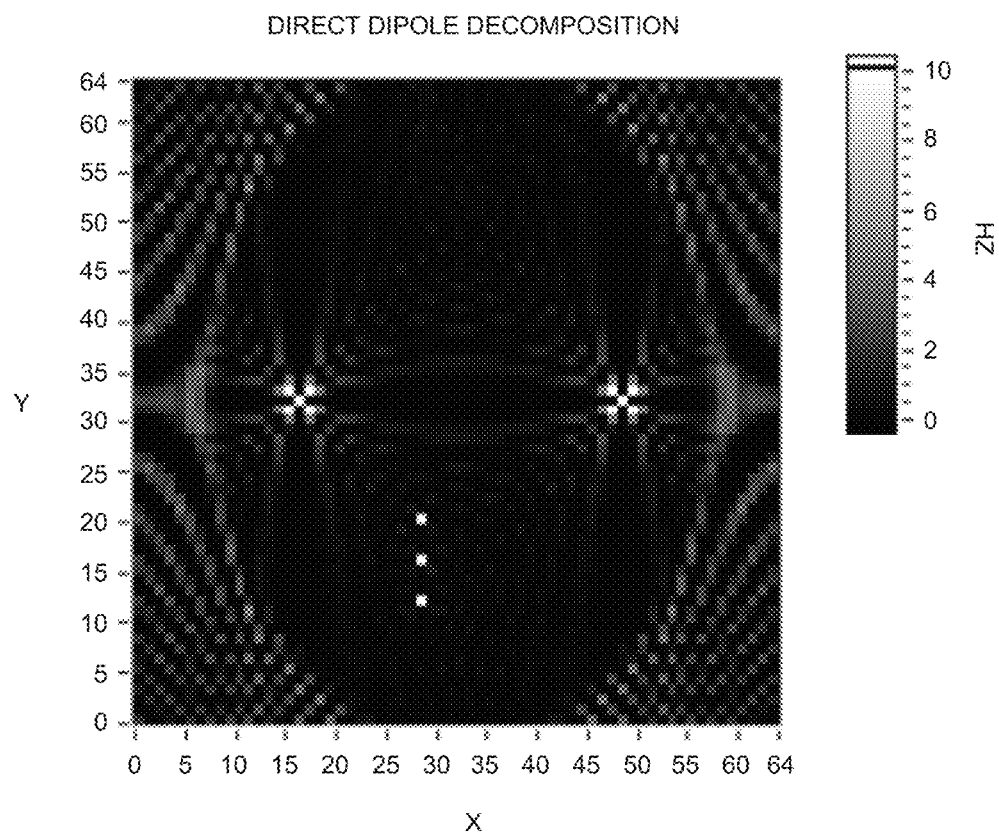
FIG. 5 illustrates one example of the results of direct dipole decomposition on a changed scale.

FIG. 5 illustrates one example of the results of direct dipole decomposition on a changed scale. The x-axis and the y-axis are in units of voxel index (4 mm voxels). The 10 Hz dipoles are clearly visible.

Figure 6:
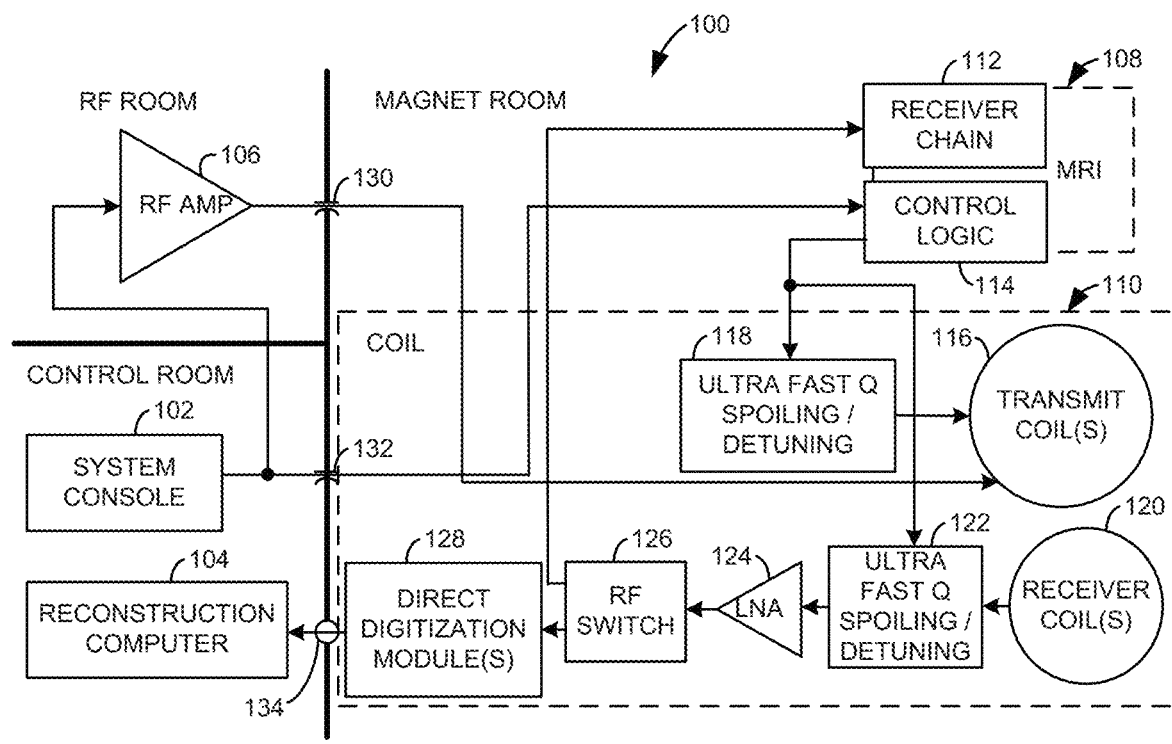
FIG. 6 is a block diagram illustrating one example of a system used to perform functional magnetic resonance imaging (fMRI).

FIG. 6 is a block diagram illustrating one example of a system 100 used to perform functional magnetic resonance imaging (fMRI) as disclosed herein. System 100 includes a control room including a system console 102 and a reconstruction computer 104. System 100 includes an RF room including an RF amplifier 106. System 100 includes a magnet room including an MRI scanner 108 and a coil 110. MRI scanner 108 includes a receiver chain 112 and control logic 114. Coil 110 includes a single transmit coil 116 or a plurality of transmits coils 116, an ultra fast Q-spoiling/detuning circuit 118, a single receiver coil 120 or a plurality of receiver coils 120, an ultra fast Q-spoiling/detuning circuit 122, a low noise amplifier (LNA) 124, an RF switch 126, and a single direct digitization module 128 or a plurality of direct digitization modules 128. In one example, the number of direct digitization modules 128 equals the number of receiver coils 120.

System console 102 is communicatively coupled to the input of RF amplifier 106 and to control logic 114 (through a filter 132) of MRI scanner 108. Filter 132 isolates the console room from the magnet room. System console 102 controls the operation of RF amplifier 106 and MRI scanner 108 to acquire MRI data of a patient. System console 102 may include a computer or other suitable processing system. The output of RF amplifier 106 is electrically coupled to an input of transmit coil(s) 116 through a filter 130. Filter 130 isolates the magnet room from the RF room.

Control logic 114 is electrically coupled to an input of ultra fast Q-spoiling/detuning circuit 118 and an input of ultra fast Q-spoiling/detuning circuit 122. Ultra fast Q-spoiling/detuning circuit 118 is electrically coupled to transmit coil(s) 116. Receiver coil(s) 120 is electrically coupled to ultra fast Q-spoiling/detuning circuit 122. Control logic 114 controls the excitation of transmit coil(s) 116.

Ultra fast Q-spoiling/detuning circuit 122 is electrically coupled to the input of LNA 124. The output of LNA 124 is electrically coupled to an input of RF switch 126. One output of RF switch 126 is electrically coupled to receiver chain 112 of MRI scanner 108, and another output of RF switch 126 is electrically coupled to an input of direct digitization module(s) 128. An output of direct digitization module(s) 128 is communicatively coupled to reconstruction computer 104 through a waveguide 134. LNA 124 provides amplified analog data acquired by receiver coil(s) 120 to RF switch 126. RF switch 126 may pass the analog data to receiver chain 112 of MRI scanner 108 or to direct digitization module(s) 128. Direct digitization module(s) 128 convert the analog data to digital data and pass the digital data to reconstruction computer 104.

The reconstruction computer 104 and the coil 110 may be used to implement this disclosure. The reconstruction computer 104 may be any device that can read in the digitized data and process the data in accordance with the dipole decomposition algorithm. While in this example the reconstruction computer 104 is a desktop workstation/computer, in other examples the reconstruction computer may be part of the system console 102. In yet other examples, the reconstruction computer 104 may be part of a cloud computing system, a dedicated server, a desktop workstation/computer, a mobile device, or another suitable open/closed source hardware and software system capable of processing the digitized data.

Figure 7:
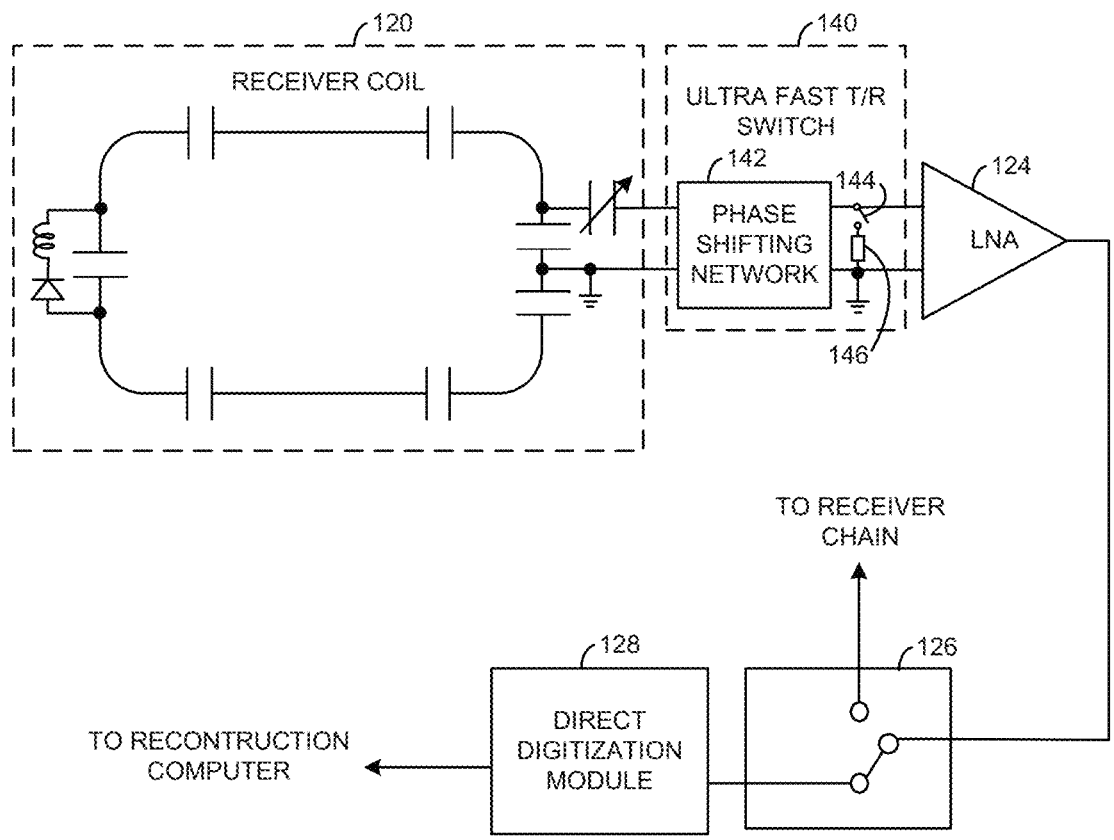
FIG. 7 is a schematic diagram illustrating one example of a receiver coil and signal processing components for the acquired signals.

FIG. 7 is a schematic diagram illustrating one example of a receiver coil 120 and signal processing components for the acquired signals. Receiver coil 120 is electrically coupled to an ultra fast T/R switch 140. The output of ultra fast T/R switch 140 is electrically coupled to the input of LNA 124. The output of LNA 124 is electrically coupled to an input of RF switch 126, and an output of RF switch 126 is electrically coupled to an input of direct digitization module 128.

The receiver coil 120 is responsible for signal reception. Similar to the transmit coil 116 described below with reference to FIG. 8, the receiver coil 120 is an LC resonator (either series or parallel) and in this example the receiver coil is an array of loop coils for whole brain coverage. Ultra fast T/R switch 140 includes a phase shifting network 142, a switch 144, and a resistive load 146. Also similar to a transmit-side T/R switch, the receive-side T/R switch is responsible for damping the receiver coil (and protecting the LNA) with coil ringdown times in under 1 µs. The topology for this T/R switch 140 may vary depending upon the application.

The RF switch 126 may be a single pole double throw switch that directs the amplified analog received signal either to the original equipment manufacturer's receiver chain 112 or to the direct digitization module 128. The RF switch 126 may be an electrical, mechanical, or electromechanical switch. In one example, the RF switch 126 is a low impedance field-effect transistor (FET).

The direct digitization module 128 may be directly responsible for digitizing the analog signal from the receiver coil 120 and transmitting the digitized signal to the reconstruction computer 104 via TCP/IP communication protocols or other suitable protocols. The direct digitization module 128, in this example, may contain, but is not limited to analog and digital filters frequency mixer with a local oscillator, an analog to digital converter, a processing unit (e.g., a central processing unit (CPU) or a field-programmable gate array (FPGA)), and a random access memory (e.g., a dynamic random access memory (DRAM)). The processing unit may communicate with the system console 102 to determine the correct time to send data to the reconstruction computer 104. If a connection to the reconstruction computer 104 cannot be secured, the processing unit may store data in the random access memory. The memory storage may be on board or a removable disk. In one example, the direct digitization module 128 is outside of the coil 110 (FIG. 6). In other examples, the direct digitization module 128 may be part of the coil 110.

Figure 8:
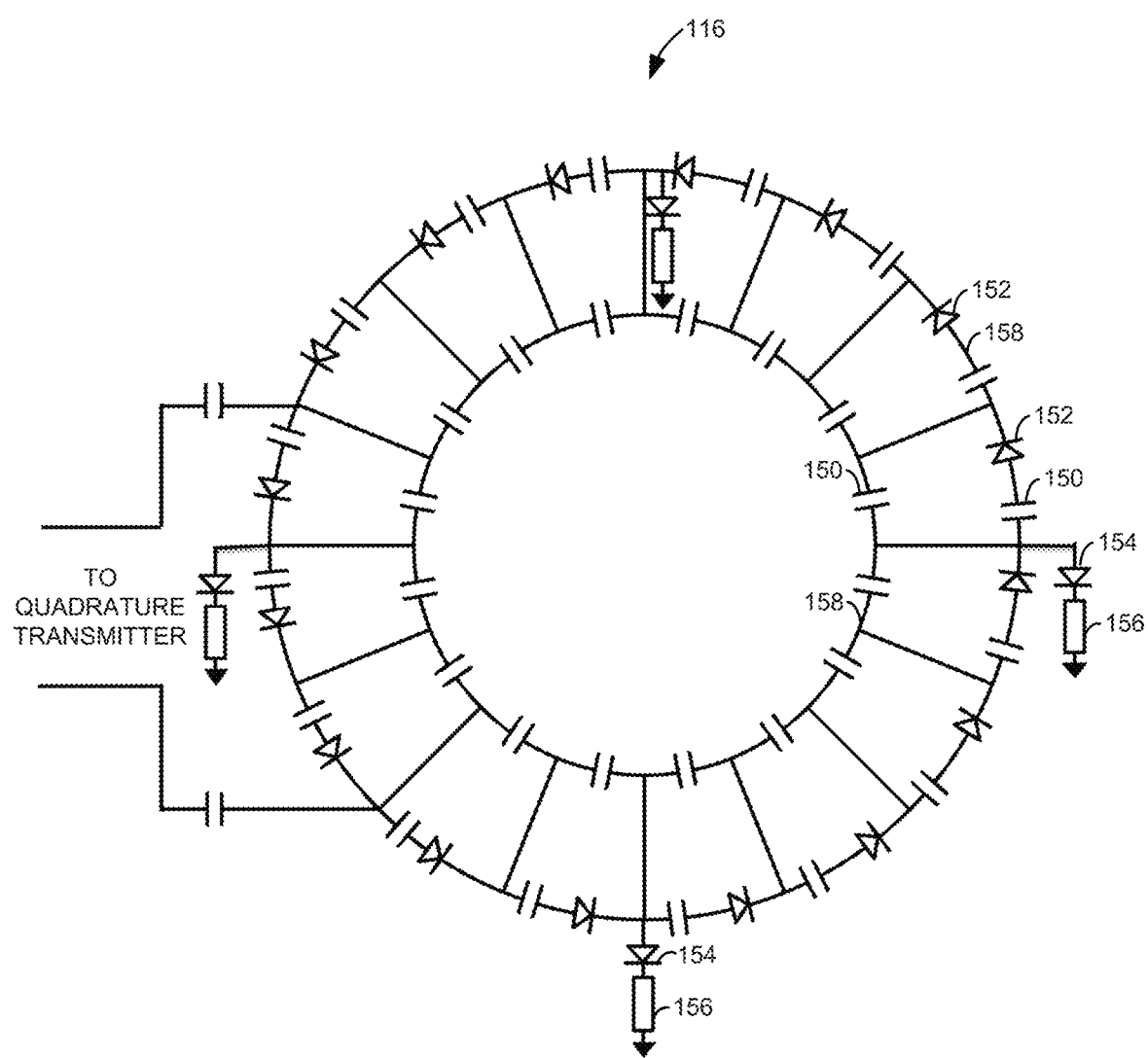
FIG. 8 illustrates one example of a transmit coil.

FIG. 8 illustrates a 2D representation of one example of a 3D birdcage transmit coil 116. The transmit coil 116 is responsible for signal excitation. Transmit coil 116 includes capacitors (e.g., capacitors 150), detuning PIN diodes (e.g., PIN diodes 152), Q-spoiling PIN diodes (e.g., PIN diodes 154), resistors (e.g., resistors 156), and inductive wire (e.g., wire 158). The transmit coil 116 is electrically coupled to a quadrature transmitter.

The transmit coil is an inductor-capacitor (LC) resonator (either series or parallel); the lumped element capacitors are chosen such that the coil will resonate at proton's larmor frequency for the field strength of the MRI. In this example, the transmit coil is a "birdcage" coil for whole brain excitation, however, the transmit coil may be a single coil, an array of coils, or a volume coil such as the birdcage or TEM. Standard methods of detuning a transmit coil during receive, namely PIN diodes on the end ring are not fast enough for ZTE imaging, therefore, Q-spoiling has been added. Q-spoiling is accomplished by adding the PIN diodes and resistive loads to ground on the end-rings. Here, in this example, the Q-spoiling is geometrically positioned on the end rings, however, they can be added at current or voltage nodes as well.

Figure 9A:
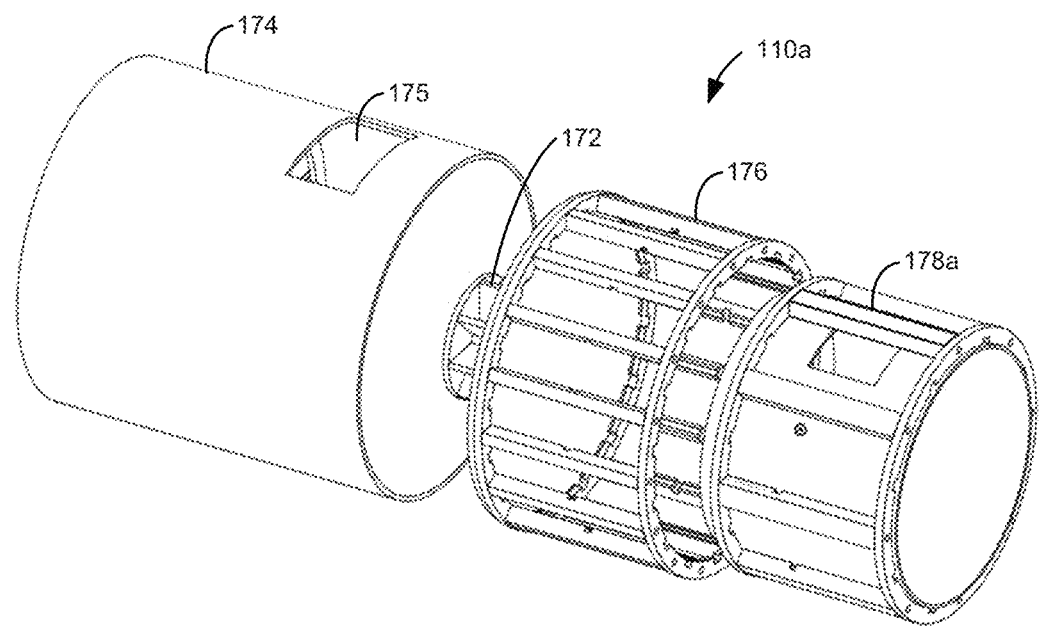
FIGS. 9A and 9B illustrate exploded views of example fMRI head coils.
Figure 9B:
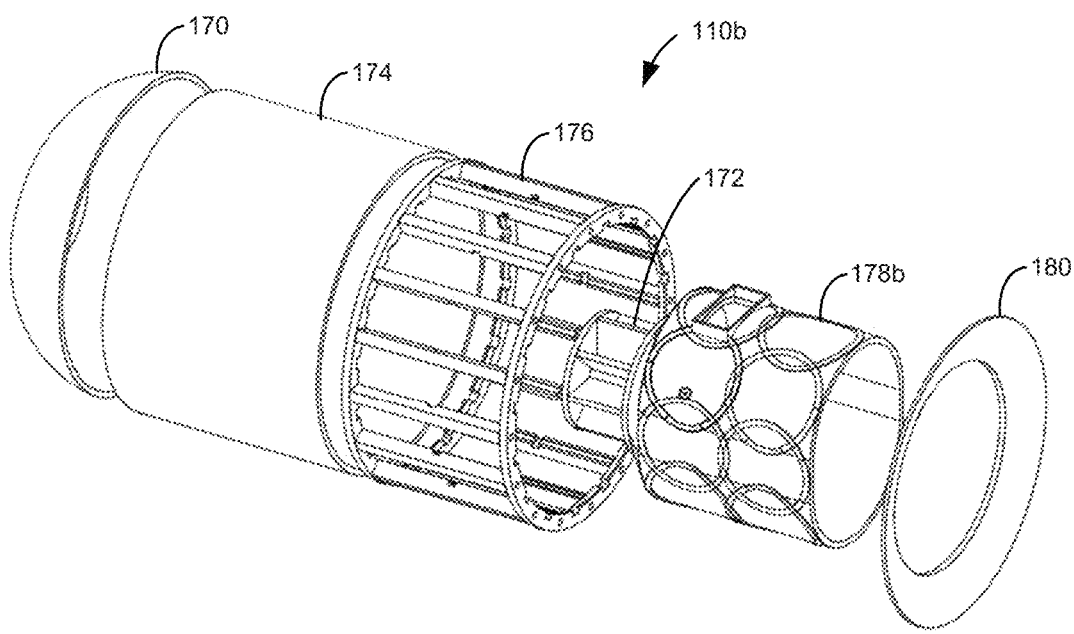

FIGS. 9A and 9B illustrate exploded views of example fMRI head coils 110a and 110b, respectively. The fMRI coil 110a includes a preamps and an RF switch assembly 172, a main housing 174 with an fMRI window 175 and slotted ground shield (not shown), a transmit-only "birdcage" coil 176, and a receiver coil 178a. The fMRI head coil 110b includes a back cap 170, preamps and an RF switch assembly 172, a main housing 174, a transmit-only "birdcage" coil 176, a receiver coil 178b, and an end cap 180. Coils 110a and 110b are made of materials that are void of protons and additional shielding is used to eliminate extraneous signals from the main housing 174, coil electronics 172, and the bore liner of the magnet. In both examples, all housing materials are chosen from a proton-free polymer (e.g., PTFE), such as from transfer molded PCTFE. The transmit coil is housed in a proton free polymer. The receiver coil can either be housed in the PTFE cage (e.g., receiver coil 178a of FIG. 9A) or directly fastened to the interior patient liner/housing (e.g., receiver coil 178b of FIG. 9B).

Figure 10:
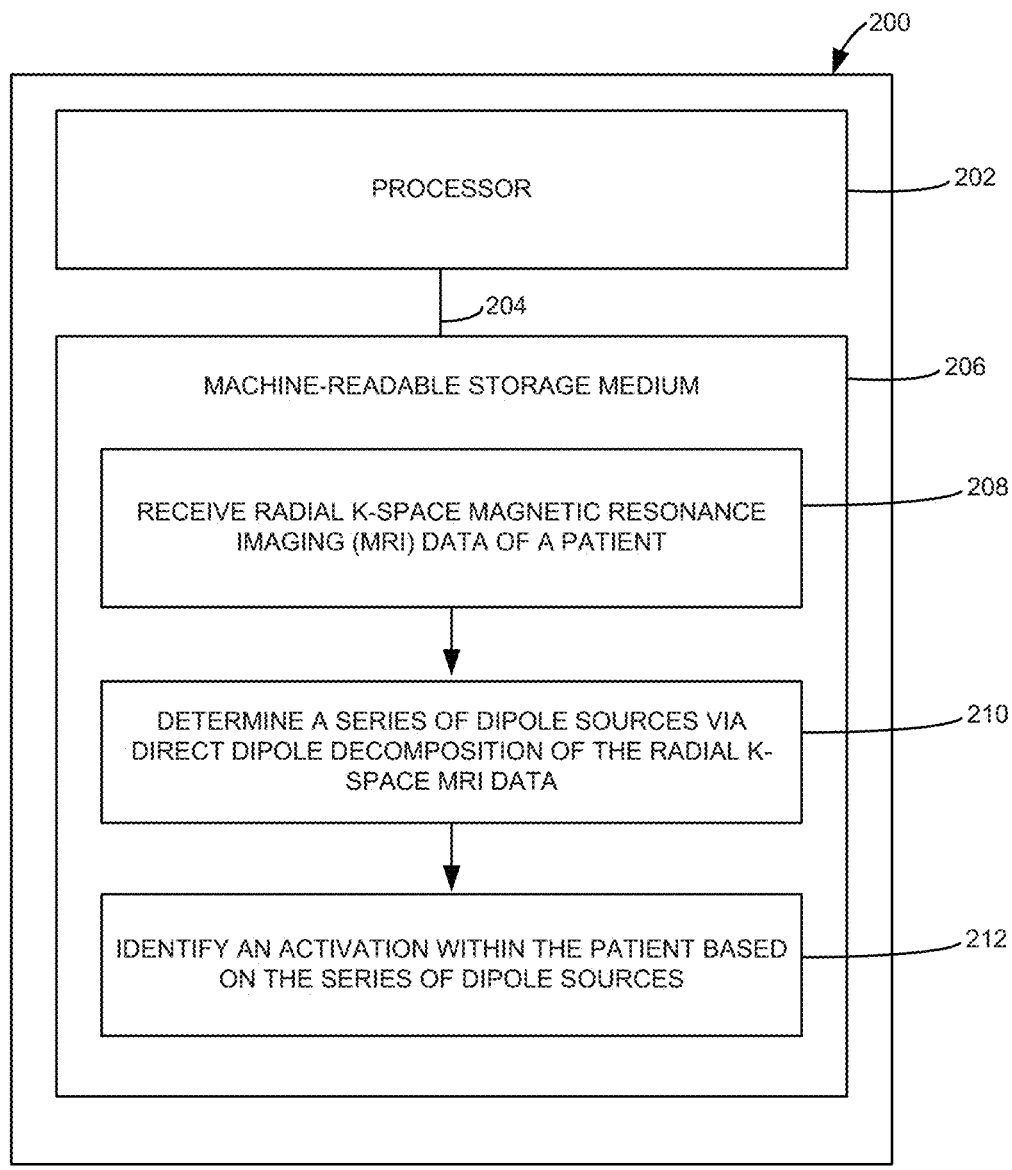
FIG. 10 is a block diagram illustrating one example of a processing system for identifying an activation within a patient.

FIG. 10 is a block diagram illustrating one example of a processing system 200 for identifying an activation within a patient. In one example, system 200 provides reconstruction computer 104 previously described and illustrated with reference to FIG. 6. System 200 includes a processor 202 and a machine-readable storage medium 206. Processor 202 is communicatively coupled to machine-readable storage medium 206 through a communication path 204. Although the following description refers to a single processor and a single machine-readable storage medium, the description may also apply to a system with multiple processors and multiple machine-readable storage mediums. In such examples, the instructions may be distributed (e.g., stored) across multiple machine-readable storage mediums and the instructions may be distributed (e.g., executed by) across multiple processors.

Processor 202 includes one (i.e., a single) central processing unit (CPU) or microprocessor or graphics processing unit (GPU) or more than one (i.e., multiple) CPU or microprocessor or GPU, and/or other suitable hardware devices for retrieval and execution of instructions stored in machine-readable storage medium 206. Processor 202 may fetch, decode, and execute instructions 208-212 to identify an activation within a patient.

Processor 202 may fetch, decode, and execute instructions 208 to receive radial k-space magnetic resonance imaging (MRI) data of a patient. In one example, the radial k-space MRI data includes radial k-space MRI data obtained via a free induction decay (FID) sequence. The FID sequence may include a sweep imaging with Fourier transformation (SWIFT) sequence or a zero echo time (ZTE) sequence. In one example, the radial k-space MRI data comprises T1 weighted radial k-space MRI data. In another example, the radial k-space MRI data comprises T2 weighted radial k-space MRI data. In yet another example, the radial k-space MRI data comprises diffusion or perfusion weighted radial k-space MRI data.

Processor 202 may fetch, decode, and execute instructions 210 to determine a series of dipole sources via direct dipole decomposition of the radial k-space MRI data. In one example, processor 202 may execute the instructions 210 to determine the series of dipole sources by determining a secular dipole basis and extracting the series of dipole sources from the radial k-space MRI data based on the secular dipole basis. In other examples, processor 202 may execute the instructions 210 to determine the series of dipole sources by decomposing the radial k-space MRI data into a series of isocenter spherical harmonics to compensate for MRI magnet and system inhomogeneities. In this case, the dipole sources may include time varying dipole sources and the isocenter spherical harmonics may include time varying spherical harmonics.

Processor 202 may fetch, decode, and execute instructions 212 to identify an activation within the patient based on the series of dipole sources. In one example, the dipole sources may include time varying dipole sources and processor 202 may execute the instructions 212 to identify an activation within the patient by performing independent component analysis on the series of time varying dipole sources. Processor 202 may execute further instructions to correct the radial k-space MRI data for object motion and field inhomogeneities and reconstruct an anatomical reference image of the patient based on the corrected radial k-space MRI data. In this case, the dipole sources may include time varying dipole sources and the processor 202 may execute the instructions to further overlay and display the time varying dipole sources over the anatomical reference image.

As an alternative or in addition to retrieving and executing instructions, processor 202 may include one (i.e., a single) electronic circuit or more than one (i.e., multiple) electronic circuit comprising a number of electronic components for performing the functionality of one of the instructions or more than one of the instructions in machine-readable storage medium 206. With respect to the executable instruction representations (e.g., boxes) described and illustrated herein, it should be understood that part or all of the executable instructions and/or electronic circuits included within one box may, in alternate examples, be included in a different box illustrated in the figures or in a different box not shown.

Machine-readable storage medium 206 is a non-transitory storage medium and may be any suitable electronic, magnetic, optical, or other physical storage device that stores executable instructions. Thus, machine-readable storage medium 206 may be, for example, random access memory (RAM), electrically erasable programmable read-only memory (EEPROM), a storage drive, an optical disc, and the like. Machine-readable storage medium 206 may be disposed within system 200, as illustrated in FIG. 10. In this case, the executable instructions may be installed on system 200. Alternatively, machine-readable storage medium 206 may be a portable, external, or remote storage medium that allows system 200 to download the instructions from the portable/external/remote storage medium. In this case, the executable instructions may be part of an installation package.

Figure 11:
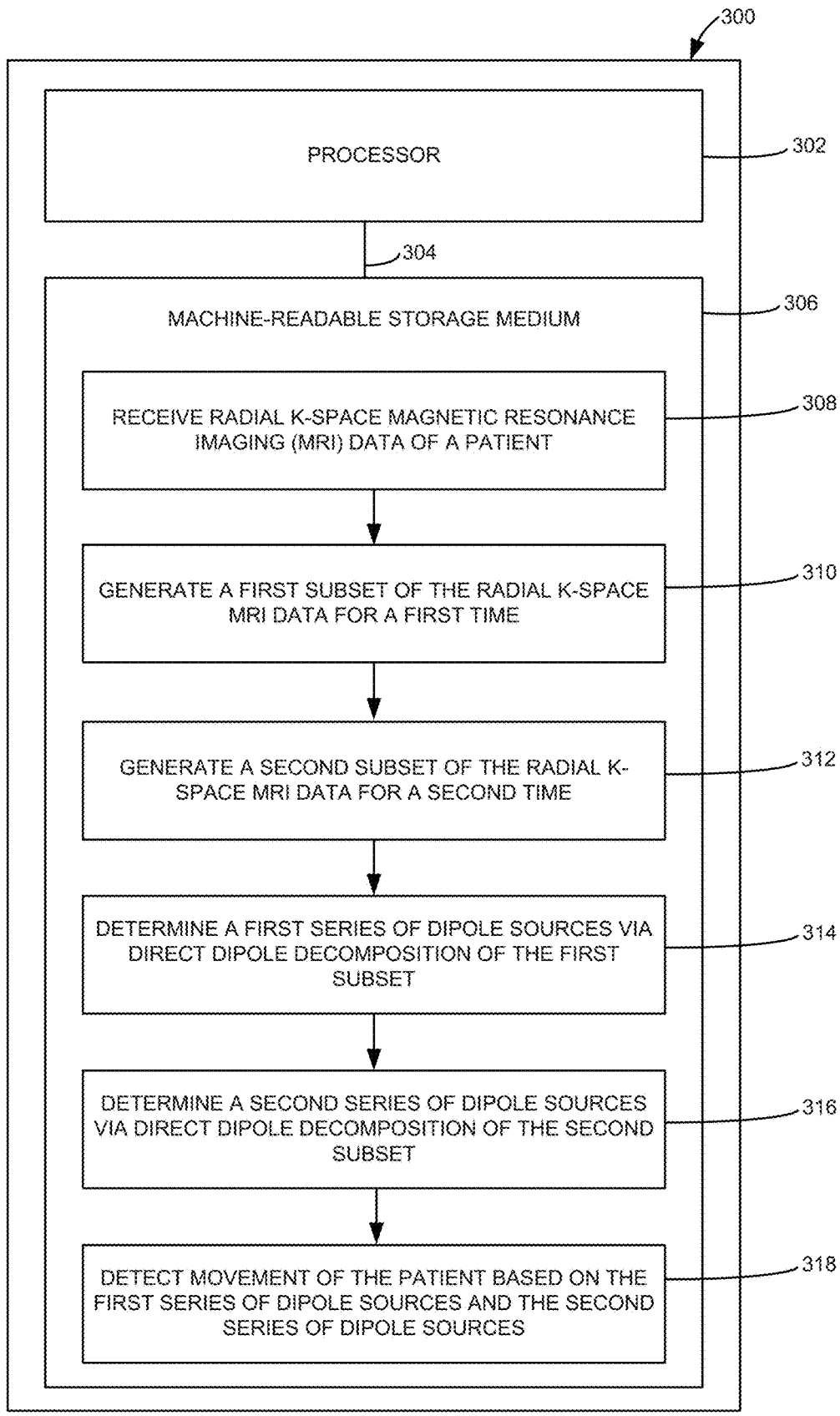
FIG. 11 is a block diagram illustrating one example of a processing system for detecting movement of a patient.

FIG. 11 is a block diagram illustrating one example of a processing system 300 for detecting movement of a patient. In one example, system 300 provides reconstruction computer 104 previously described and illustrated with reference to FIG. 6. System 300 includes a processor 302 and a machine-readable storage medium 306. Processor 302 is communicatively coupled to machine-readable storage medium 306 through a communication path 304. Although the following description refers to a single processor and a single machine-readable storage medium, the description may also apply to a system with multiple processors and multiple machine-readable storage mediums. In such examples, the instructions may be distributed (e.g., stored) across multiple machine-readable storage mediums and the instructions may be distributed (e.g., executed by) across multiple processors.

Processor 302 includes one (i.e., a single) CPU or microprocessor or GPU or more than one (i.e., multiple) CPU or microprocessor or GPU, and/or other suitable hardware devices for retrieval and execution of instructions stored in machine-readable storage medium 306. Processor 302 may fetch, decode, and execute instructions 308-318 to detect movement of a patient.

Processor 302 may fetch, decode, and execute instructions 308 to receive radial k-space magnetic resonance imaging (MRI) data of a patient. In one example, the radial k-space MRI data includes radial k-space MRI data obtained via a free induction decay (FID) sequence. The FID sequence may include a sweep imaging with Fourier transformation (SWIFT) sequence or a zero echo time (ZTE) sequence.

Processor 302 may fetch, decode, and execute instructions 310 to generate a first subset of the radial k-space MRI data for a first time. Processor 302 may fetch, decode, and execute instructions 312 to generate a second subset of the radial k-space MRI data for a second time. Processor 302 may fetch, decode, and execute instructions 314 to determine a first series of dipole sources via direct dipole decomposition of the first subset. Processor 302 may fetch, decode, and execute instructions 316 to determine a second series of dipole sources via direct dipole decomposition of the second subset. Processor 302 may fetch, decode, and execute instructions 318 to detect movement of the patient based on the first series of dipole sources and the second series of dipole sources. In one example, processor 302 may execute further instructions to correct the radial k-space MRI data based on the detected movement.

As an alternative or in addition to retrieving and executing instructions, processor 302 may include one (i.e., a single) electronic circuit or more than one (i.e., multiple) electronic circuit comprising a number of electronic components for performing the functionality of one of the instructions or more than one of the instructions in machine-readable storage medium 306. With respect to the executable instruction representations (e.g., boxes) described and illustrated herein, it should be understood that part or all of the executable instructions and/or electronic circuits included within one box may, in alternate examples, be included in a different box illustrated in the figures or in a different box not shown.

Machine-readable storage medium 306 is a non-transitory storage medium and may be any suitable electronic, magnetic, optical, or other physical storage device that stores executable instructions. Thus, machine-readable storage medium 306 may be, for example, RAM, EEPROM, a storage drive, an optical disc, and the like. Machine-readable storage medium 306 may be disposed within system 300, as illustrated in FIG. 11. In this case, the executable instructions may be installed on system 300. Alternatively, machine-readable storage medium 306 may be a portable, external, or remote storage medium that allows system 300 to download the instructions from the portable/external/remote storage medium. In this case, the executable instructions may be part of an installation package.

Figure 12:
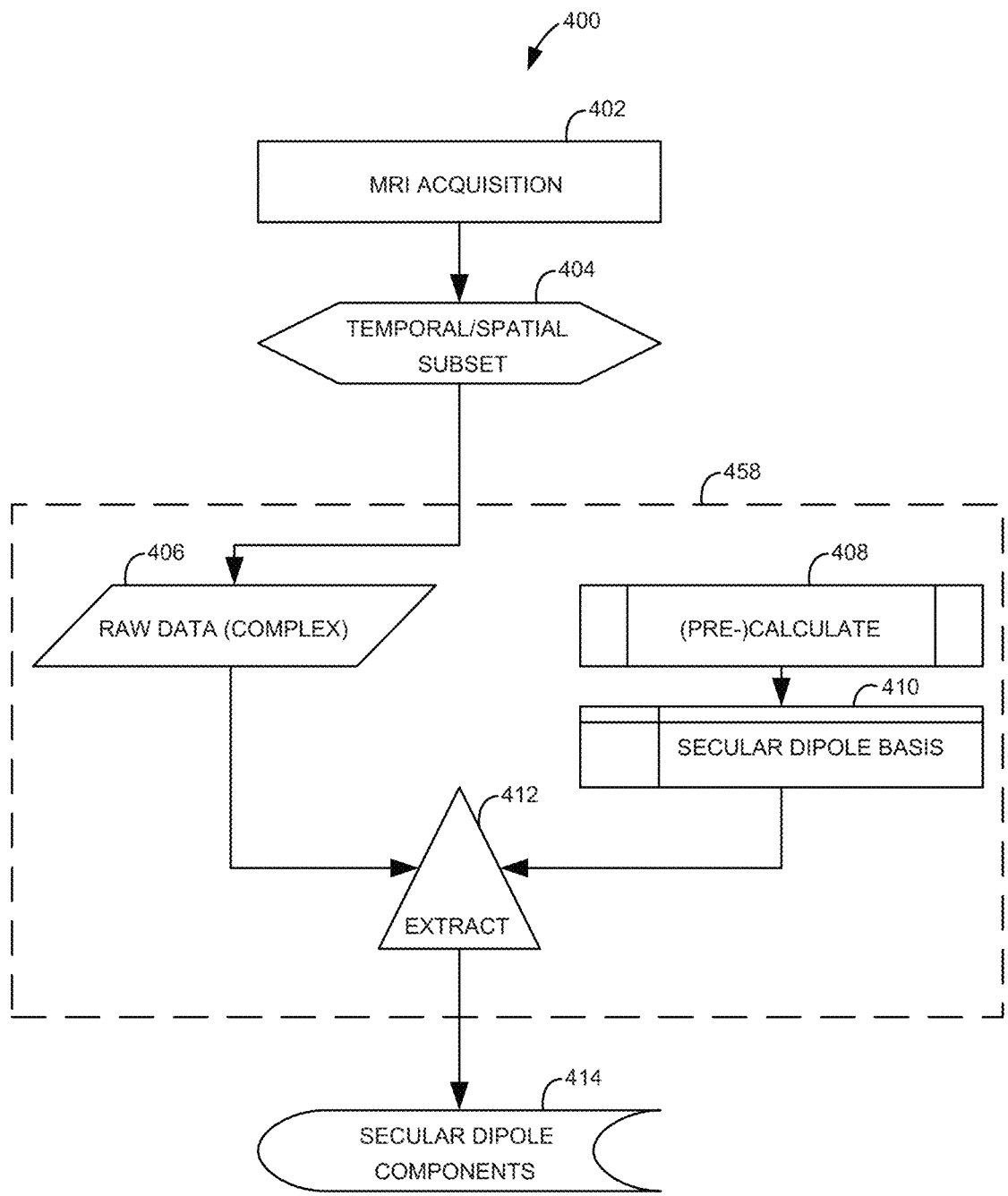
FIG. 12 is a flow diagram illustrating one example of a method for direct dipole decomposition.

FIG. 12 is a flow diagram illustrating one example of a method 400 for direct dipole decomposition. At 402, method 400 includes an MRI acquisition. A subset of the data obtained in the MRI acquisition is generated at 404 to provide a temporal/spatial subset. The raw data (complex) 406 generated at 404 is input to a direct dipole decomposition process 458. At 408, a secular dipole basis is calculated or precalculated (e.g., via equation 3) to provide the secular dipole basis at 410. At 412, method 400 includes extracting a series of dipole sources from the raw data 406 based on the secular dipole basis 410 (e.g., via equation 5). The secular dipole components are then output at 414.

Figure 13:
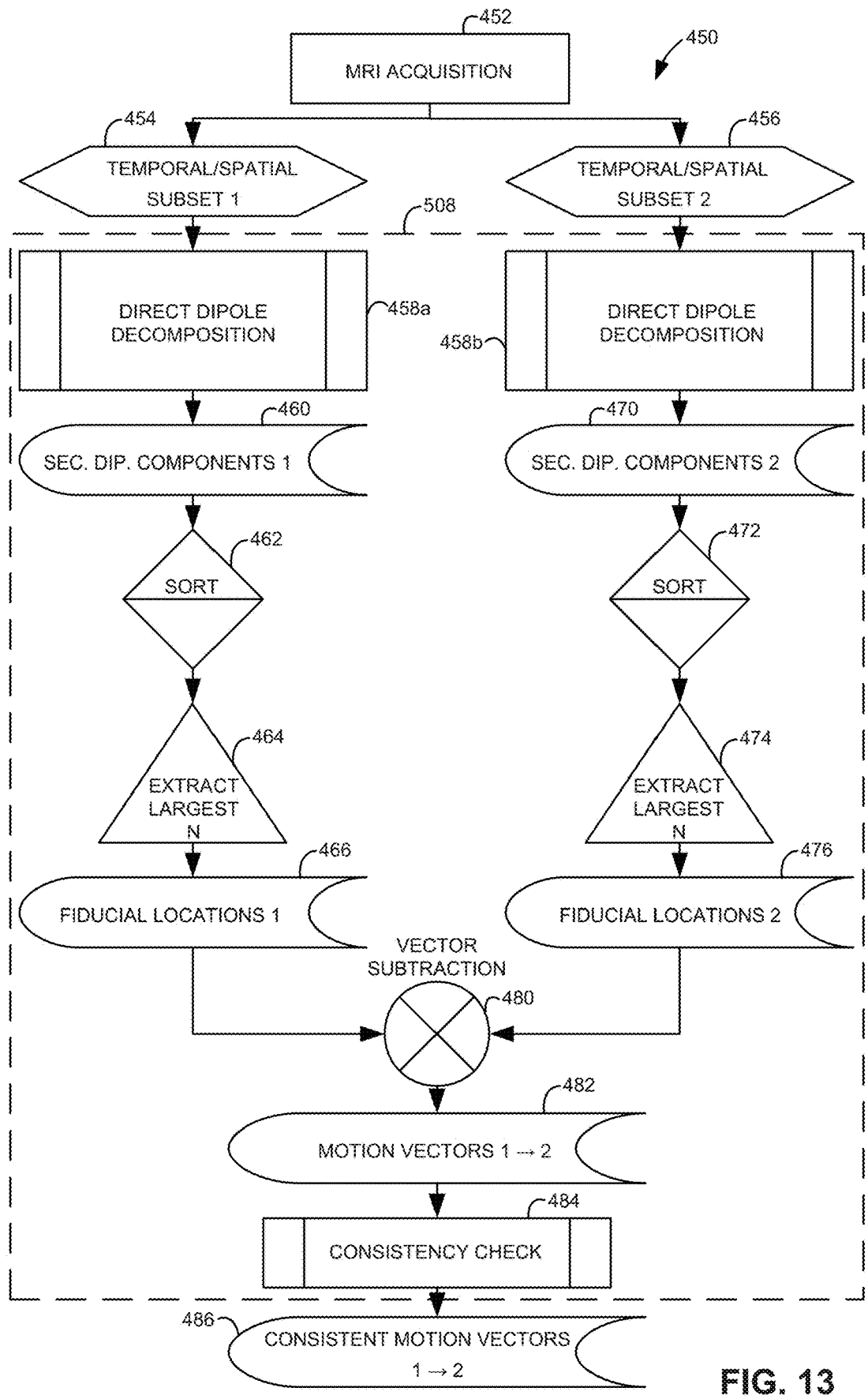
FIG. 13 is a flow diagram illustrating one example of a method for direct dipole decomposition motion estimation.

FIG. 13 is a flow diagram illustrating one example of a method 450 for direct dipole decomposition motion estimation. At 452, method 450 includes an MRI acquisition. A first subset of the data obtained in the MRI acquisition is generated at 454 to provide a first temporal/spatial subset. A second subset of the data obtained in the MRI acquisition is generated at 456 to provide a second temporal/spatial subset. Direct dipole decomposition 458a (indicated at 458 in FIG. 12) is performed on the first subset to provide first secular dipole components at 460. The first secular dipole components are sorted at 462 (e.g., by strength and/or location) and the largest components are extracted at 464 to output first fiducial locations at 466.

Likewise, direct dipole decomposition 458b (indicated at 458 in FIG. 12) is performed on the second subset to provide second secular dipole components at 470. The second secular dipole components are sorted at 472 (e.g., by strength and/or location) and the largest components are extracted at 474 to output second fiducial locations at 476. At 480, method 450 includes vector subtraction of the first fiducial locations and the second fiducial locations to identify motion vectors, which are output at 482. At 484, method 450 includes a consistency check to identify components that moved together to output consistent motion vectors at 486.

Figure 14:
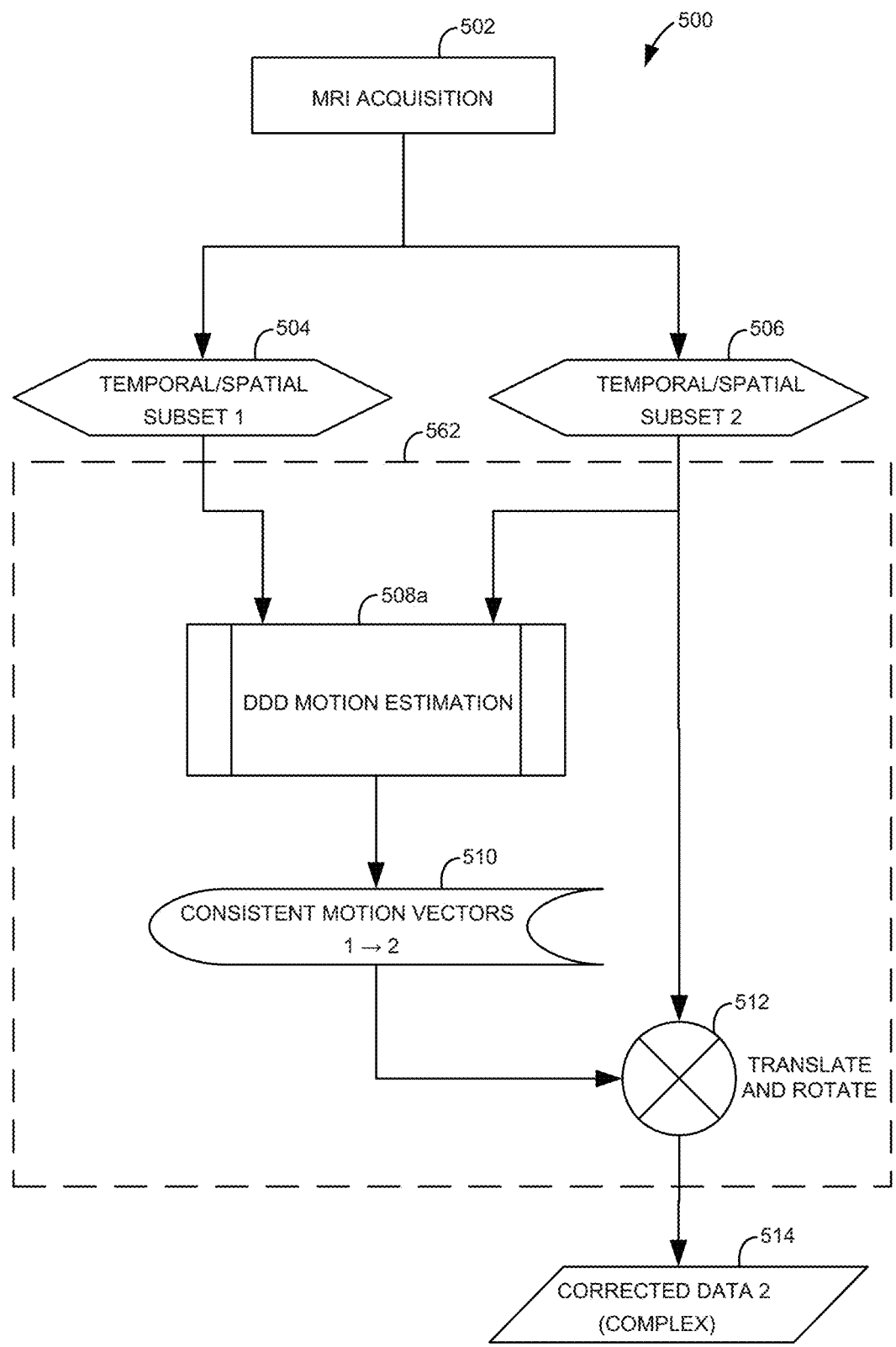
FIG. 14 is a flow diagram illustrating one example of a method for direct dipole decomposition motion correction.

FIG. 14 is a flow diagram illustrating one example of a method 500 for direct dipole decomposition motion correction. At 502, method 500 includes an MRI acquisition. A first subset of the data obtained in the MRI acquisition is generated at 504 to provide a first temporal/spatial subset. A second subset of the data obtained in the MRI acquisition is generated at 506 to provide a second temporal/spatial subset. Direct dipole decomposition motion estimation 508a (indicated at 508 in FIG. 13) is performed on the first subset and the second subset to output consistent motion vectors at 510. At 512, the second subset is translated and rotated based on the consistent motion vectors to output corrected data (complex) for the second subset at 514.

Figure 15:
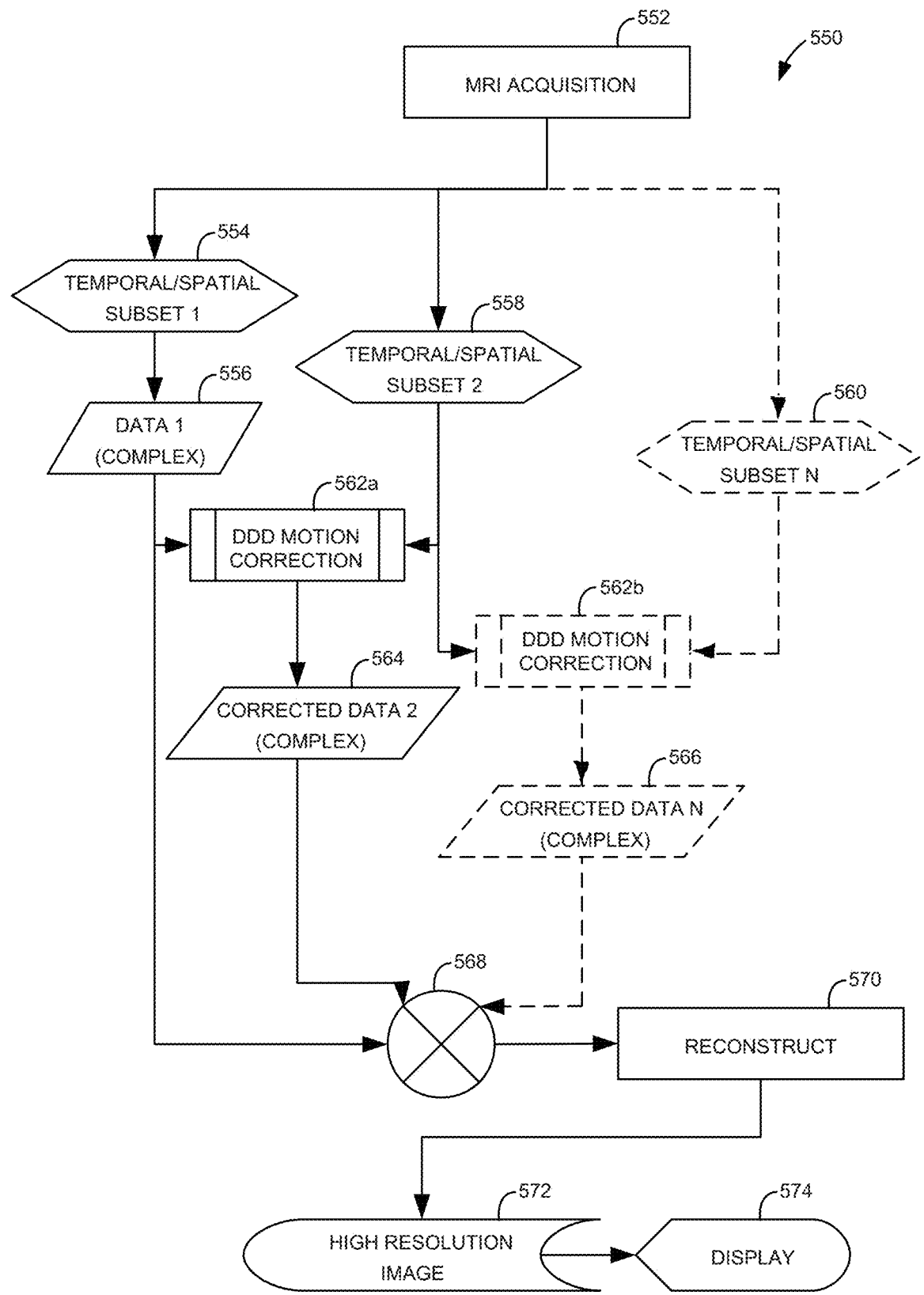
FIG. 15 is a flow diagram illustrating one example of a method for direct dipole decomposition motion corrected high-resolution image reconstruction.

FIG. 15 is a flow diagram illustrating one example of a method 550 for direct dipole decomposition motion corrected high-resolution image reconstruction. At 552, method 550 includes an MRI acquisition. A first subset of the data obtained in the MRI acquisition is generated at 554 to provide a first temporal/spatial subset and first data (complex) at 556. A second subset of the data obtained in the MRI acquisition is generated at 558 to provide a second temporal/spatial subset. Additional subsets of the data obtained in the MRI acquisition are generated up to an $N^{th}$ subset at 560 to provide N temporal/spatial subsets.

Direct dipole decomposition motion correction 562a (indicated at 562 in FIG. 14) is performed on the first subset and the second subset to output corrected second data (complex) at 564. Likewise, direct dipole decomposition motion correction is performed on the remaining subsets such that in this example direct dipole decomposition motion correction is performed on the second subset and the $N^{th}$ subset at 562b (indicated at 562 in FIG. 14) to output corrected $N^{th}$ data (complex) at 566. The first data and the corrected data is combined at 568. At 570, the combined data is used to reconstruct a high resolution image, which is output at 572. The high resolution image may be displayed at 574.

Figure 16:
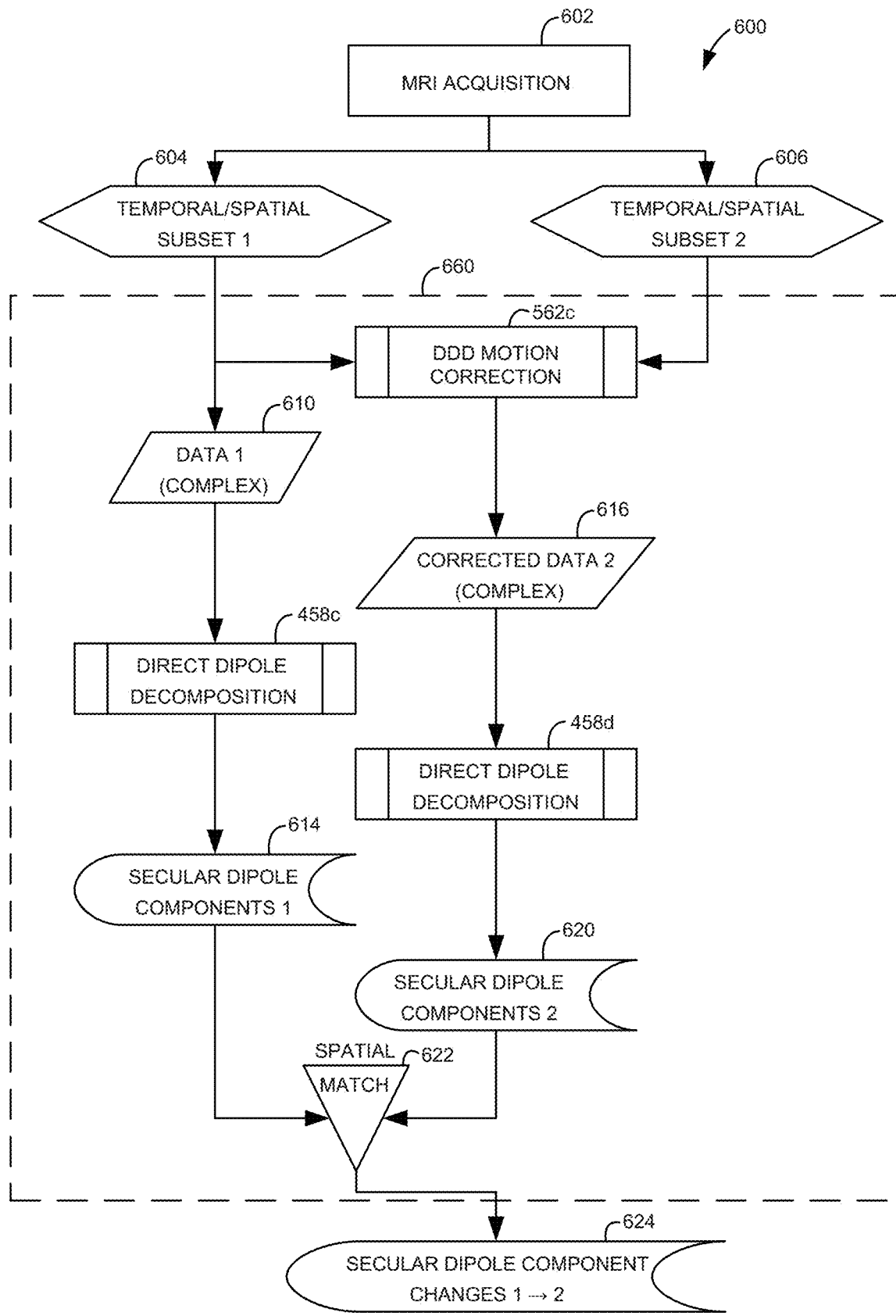
FIG. 16 is a flow diagram illustrating one example of a method for direct dipole decomposition functional estimation.

FIG. 16 is a flow diagram illustrating one example of a method 600 for direct dipole decomposition functional estimation. At 602, method 600 includes an MRI acquisition. A first subset of the data obtained in the MRI acquisition is generated at 604 to provide a first temporal/spatial subset and first data (complex) at 610. A second subset of the data obtained in the MRI acquisition is generated at 606 to provide a second temporal/spatial subset. Direct dipole decomposition motion correction 562c (indicated at 562 in FIG. 14) is performed on the first subset and the second subset to output second corrected data at 616. Direct dipole decomposition 458c (indicated at 458 in FIG. 12) is performed on the first data to output first secular dipole components at 614. Direct dipole decomposition 458d (indicated by 458 in FIG. 12) is performed on the second corrected data to output second secular dipole components at 620. At 622, method 600 includes determining a spatial match between the first secular dipole components and the second secular dipole components to identify secular dipole component changes, which are output at 624.

Figure 17:
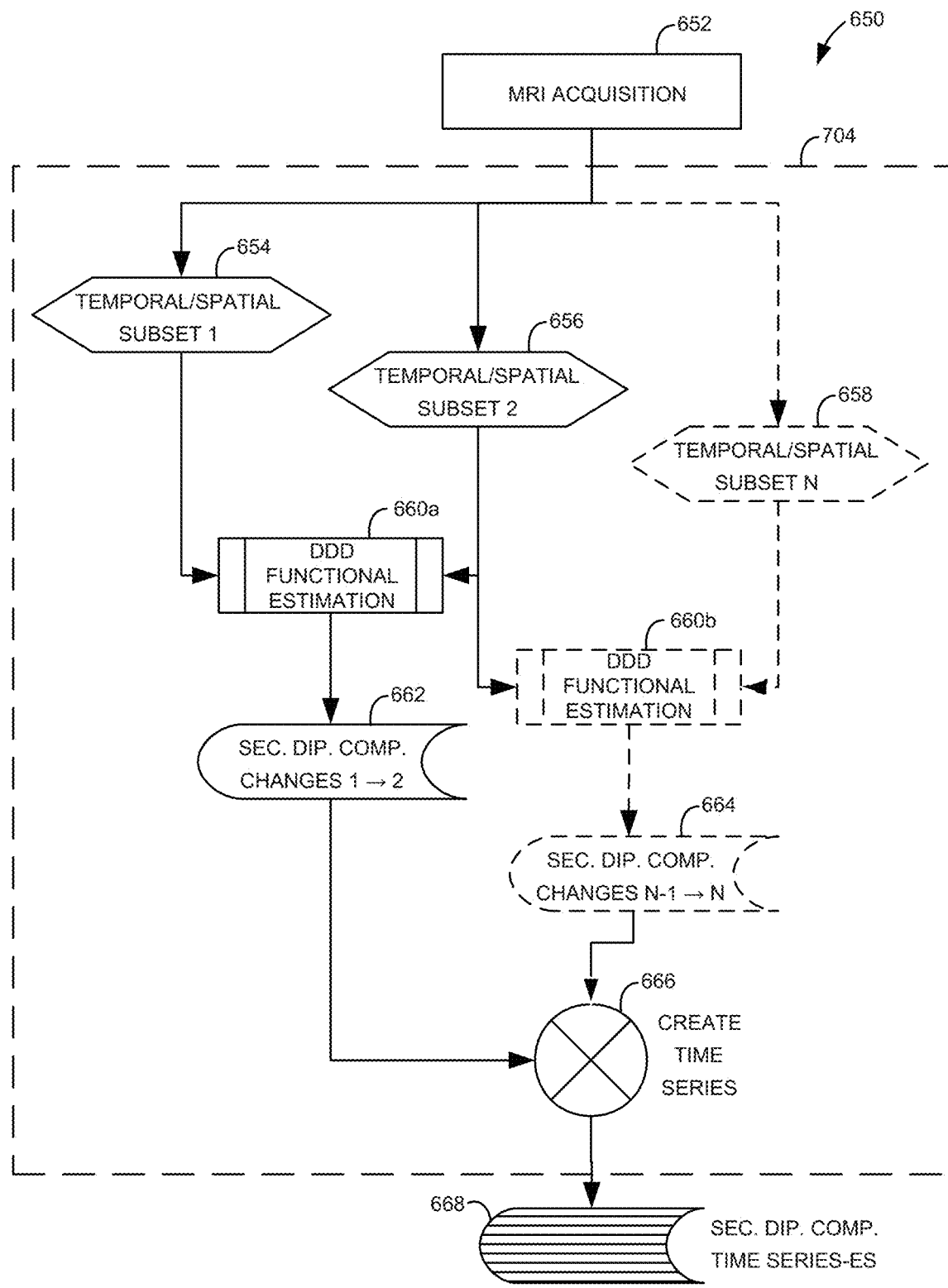
FIG. 17 is a flow diagram illustrating one example of a method for generating a direct dipole decomposition functional time series.

FIG. 17 is a flow diagram illustrating one example of a method 650 for generating a direct dipole decomposition functional time series. At 652, method 650 includes an MRI acquisition. A first subset of the data obtained in the MRI acquisition is generated at 654 to provide a first temporal/spatial subset. A second subset of the data obtained in the MRI acquisition is generated at 656 to provide a second temporal/spatial subset. Additional subsets of the data obtained in the MRI acquisition are generated up to an $N^{th}$ subset at 658 to provide N temporal/spatial subsets.

Direct dipole decomposition functional estimation 660a (indicated at 660 in FIG. 16) is performed on the first subset and the second subset to identify first secular dipole component changes at 662. Likewise, direct dipole decomposition functional estimation is performed on the remaining subsets such that in this example direct dipole decomposition functional estimation is performed on the second subset and the $N^{th}$ subset at 660b (indicated at 660 in FIG. 16) to provide $N^{th}$ secular dipole component changes at 664. At 666, the secular dipole component changes are combined to create a secular dipole component time series, which is output at 668.

Figure 18:
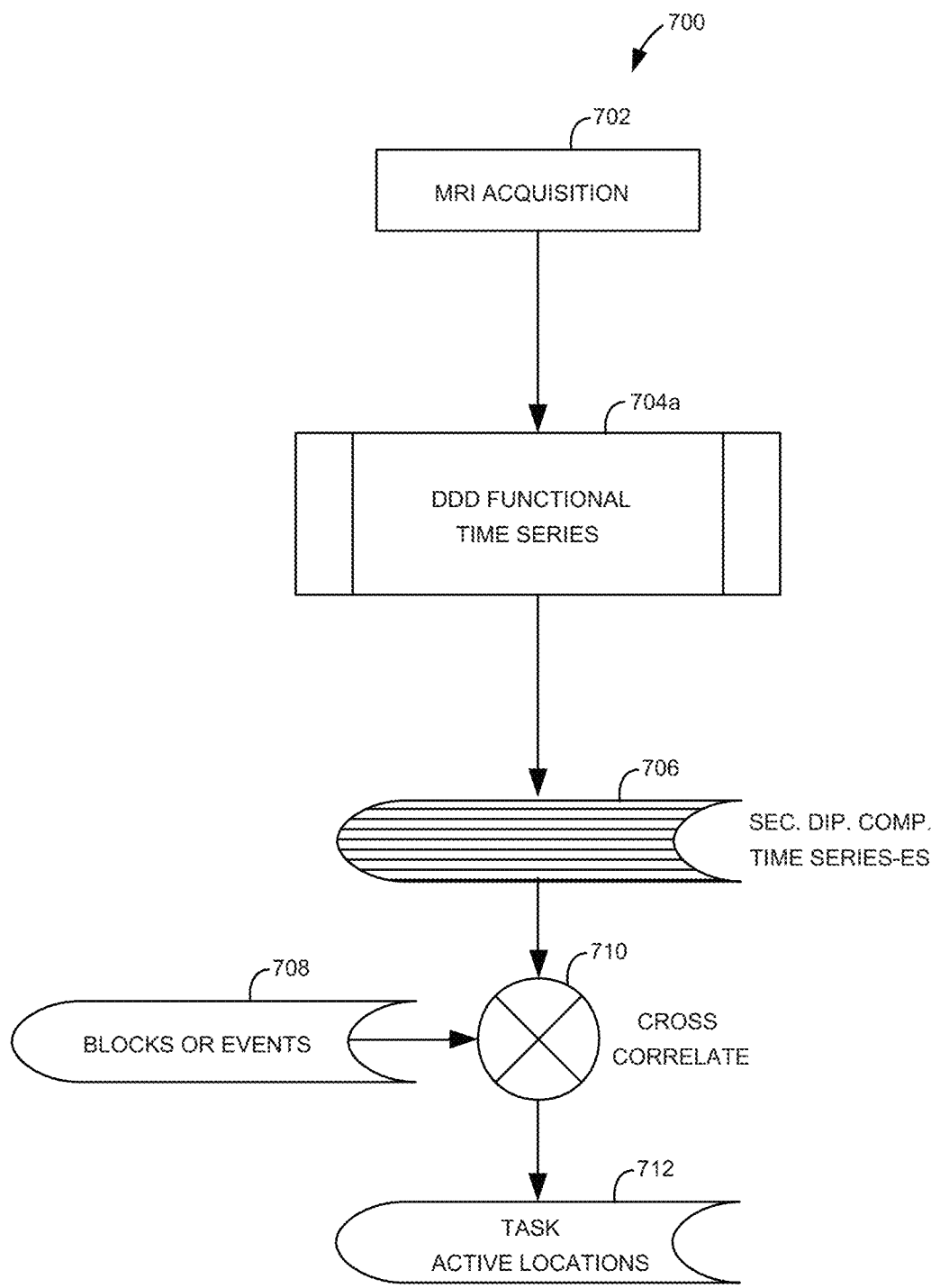
FIG. 18 is a flow diagram illustrating one example of a method for direct dipole decomposition functional time series task (block or event) processing.

FIG. 18 is a flow diagram illustrating one example of a method 700 for direct dipole decomposition functional time series task (block or event) processing. At 702, method 700 includes an MRI acquisition. Direct dipole decomposition functional time series identification 704a (indicated at 704 in FIG. 17) is performed on the MRI acquisition data to output a secular dipole component time series at 706. At 710, method 700 includes cross correlating the secular dipole component time series with blocks or events (e.g., physical actions or stimulations of the patient) 708 to identify task active locations at 712.

Figure 19:
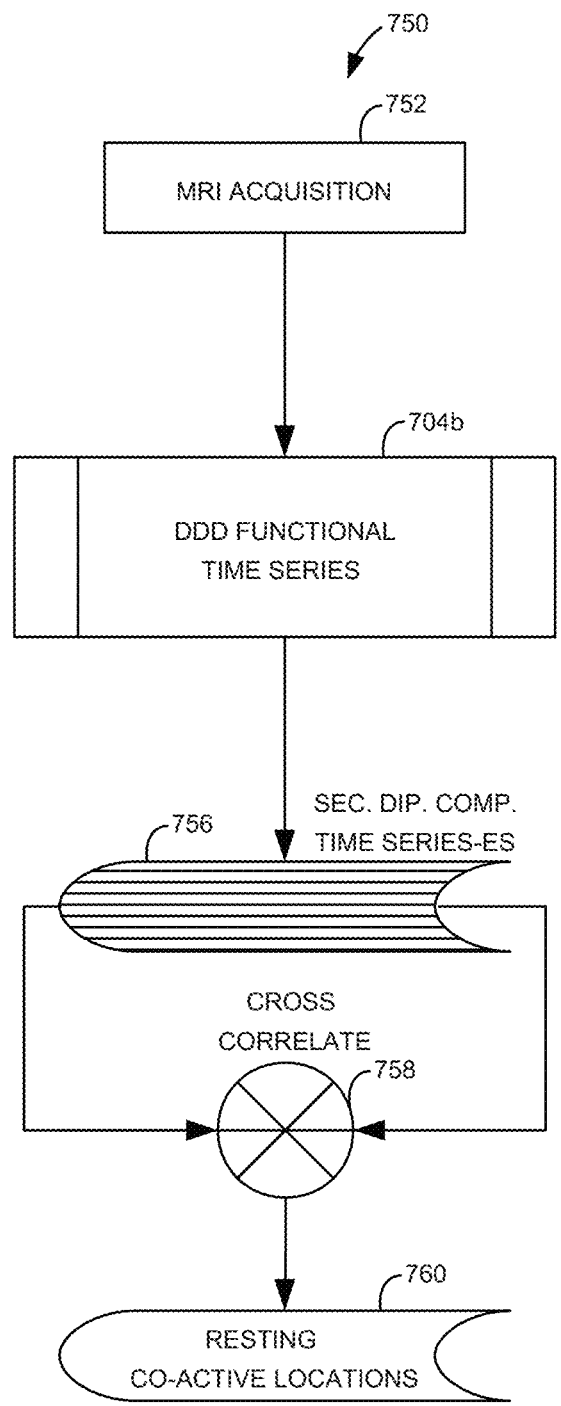
FIG. 19 is a flow diagram illustrating one example of a method for direct dipole decomposition functional time series spontaneous correlations (resting state) processing.

FIG. 19 is a flow diagram illustrating one example of a method 750 for direct dipole decomposition functional time series spontaneous correlations (resting state) processing. At 752, method 750 includes an MRI acquisition. Direct dipole decomposition functional time series identification 704b (indicated at 704 in FIG. 17) is performed on the MRI acquisition data to output a secular dipole component time series at 756. At 758, method 750 includes cross correlating the secular dipole component time series to itself to identify resting co-active locations at 760.

Figure 20:
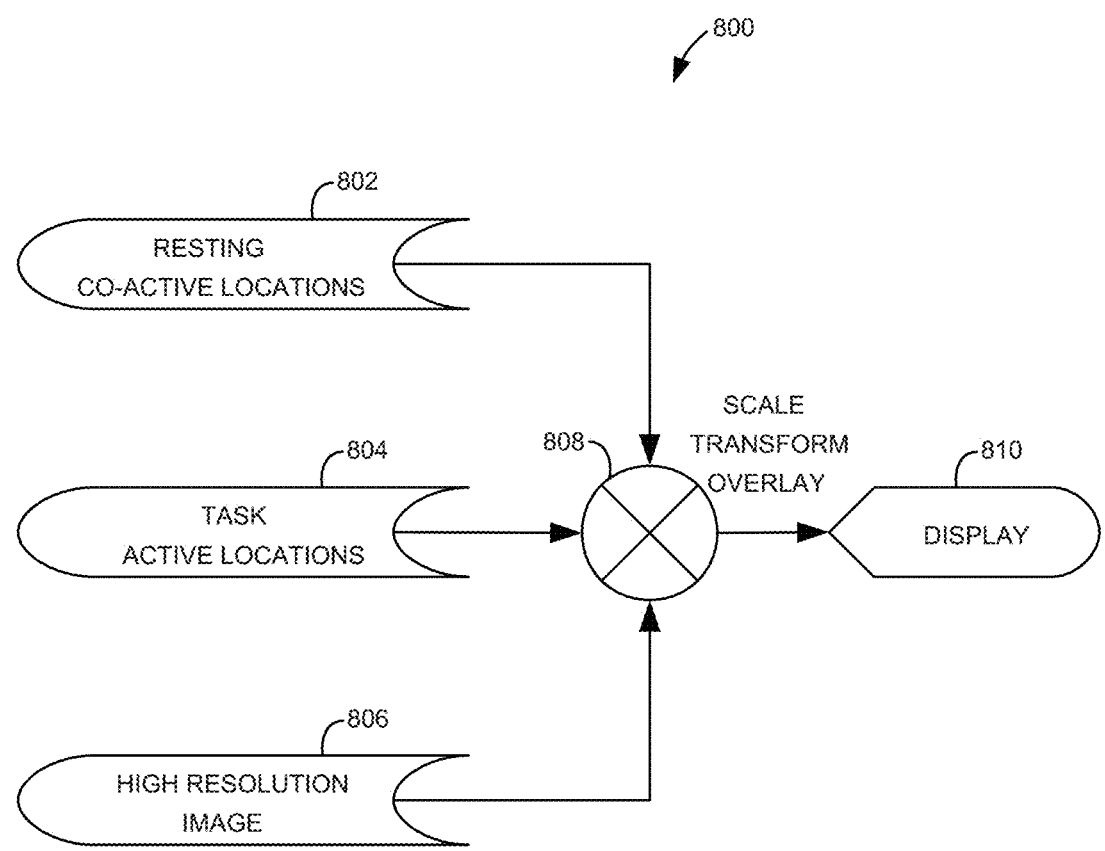
FIG. 20 is a flow diagram illustrating one example of a method for direct dipole decomposition functional and anatomical image overlay and display.

FIG. 20 is a flow diagram illustrating one example of a method 800 for direct dipole decomposition functional and anatomical image overlay and display. At 808, method 800 includes scaling, transforming, and overlaying resting co-active locations 802, task active locations 804, and a high resolution image 806 for output to a display 810.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A system comprising:
a machine readable storage medium storing instructions; and
a processor to execute the instructions to:
receive radial k-space magnetic resonance imaging (MRI) data of a patient;
determine a series of dipole sources via direct dipole decomposition of the radial k-space MRI data by determining a secular dipole basis and extracting the series of dipole sources from the radial k-space MRI data based on the secular dipole basis; and
identify an activation within the patient based on the series of dipole sources.

2. The system of claim 1, wherein the radial k-space MRI data comprises radial k-space MRI data obtained via a free induction decay (FID) sequence.

3. The system of claim 2, wherein the FID sequence comprises a sweep imaging with Fourier transformation (SWIFT) sequence or a zero echo time (ZTE) sequence.

4. The system of claim 1, wherein the processor is to execute the instructions to determine the series of dipole sources by decomposing the radial k-space MRI data into a series of isocenter spherical harmonics to compensate for MRI magnet and system inhomogeneities.

5. The system of claim 4, wherein the dipole sources comprise time varying dipole sources and the isocenter spherical harmonics comprise time varying spherical harmonics.

6. The system of claim 1, wherein the dipole sources comprise time varying dipole sources, and
wherein the processor is to execute the instructions to identify an activation within the patient by performing independent component analysis on the series of time varying dipole sources.

7. The system of claim 1, wherein the processor is to execute the instructions to further:
correct the radial k-space MRI data for object motion and field inhomogeneities; and
reconstruct an anatomical reference image of the patient based on the corrected radial k-space MRI data.

8. The system of claim 7, wherein the dipole sources comprise time varying dipole sources; and
wherein the processor is to execute the instructions to further overlay and display the time varying dipole sources over the anatomical reference image.

9. The system of claim 1, wherein the radial k-space MRI data comprises T1 weighted radial k-space MRI data.

10. The system of claim 1, wherein the radial k-space MRI data comprises T2 weighted radial k-space MRI data.

11. The system of claim 1, wherein the radial k-space MRI data comprises diffusion or perfusion weighted radial k-space MRI data.

12. A system comprising:
a machine readable storage medium storing instructions; and
a processor to execute the instructions to:
receive radial k-space magnetic resonance imaging (MRI) data of a patient;
generate a first subset of the radial k-space MRI data for a first time;
generate a second subset of the radial k-space MRI data for a second time;
determine a first series of dipole sources via direct dipole decomposition of the first subset;
determine a second series of dipole sources via direct dipole decomposition of the second subset; and
detect movement of the patient based on the first series of dipole sources and the second series of dipole sources.

13. The system of claim 12, wherein the processor is to execute the instructions to further correct the radial k-space MRI data based on the detected movement.

14. The system of claim 12, wherein the radial k-space MRI data comprises radial k-space MRI data obtained via a free induction decay (FID) sequence.

15. The system of claim 14, wherein the FID sequence comprises a sweep imaging with Fourier transformation (SWIFT) sequence or a zero echo time (ZTE) sequence.

16. A coil for a magnetic resonance imaging (MRI) system, the coil comprising:
a transmit coil;
a receiver coil;
a housing comprising a low proton background material enclosing the transmit coil and the receiver coil; and
an ultra fast transmit/receive switch electrically coupled to the receiver coil for damping the receiver coil with coil ringdown times in under 1 microsecond.

17. The coil of claim 16, further comprising:
a first Q-spoiling and detuning circuit electrically coupled to the transmit coil; and
a second Q-spoiling and detuning circuit electrically coupled to the receiver coil.

18. The coil of claim 16, further comprising:
a direct digitization module to receive analog signals from the receiver coil and convert the analog signals to digital signals.

19. The coil of claim 18, further comprising:
a radio frequency (RF) switch between the receiver coil and the direct digitization module, the RF switch controllable to pass the analog signals from the receiver coil to a selected one of a receiver chain and the direct digitization module.

20. The coil of claim 16, wherein the housing comprises a proton free material.

* * * * *